United States Patent
Utharala et al.

(10) Patent No.: US 10,745,741 B2
(45) Date of Patent: Aug. 18, 2020

(54) CELL BARCODING IN MICROFLUIDICS

(71) Applicant: EUROPEAN MOLECULAR BIOLOGY LABORATORY, Heidelberg (DE)

(72) Inventors: Ramesh Utharala, Heidelberg (DE); Chawaree Chaipan, Heidelberg (DE); Lukas Nögel, Heidelberg (DE); Christoph A. Merten, Heidelberg (DE)

(73) Assignee: EUROPEAN MOLECULAR BIOLOGY LABORATORY, Heidelberg (DE)

( * ) Notice: Subject to any disclaimer, the term of this patent is extended or adjusted under 35 U.S.C. 154(b) by 116 days.

(21) Appl. No.: 15/579,834

(22) PCT Filed: Jun. 27, 2016

(86) PCT No.: PCT/EP2016/064877
§ 371 (c)(1),
(2) Date: Dec. 5, 2017

(87) PCT Pub. No.: WO2016/207441
PCT Pub. Date: Dec. 29, 2016

(65) Prior Publication Data
US 2018/0355407 A1 Dec. 13, 2018

(30) Foreign Application Priority Data

Jun. 26, 2015 (EP) .................................. 15174088

(51) Int. Cl.
*C12Q 1/68* (2018.01)
*B01L 3/00* (2006.01)
*C12Q 1/6806* (2018.01)
*B01L 7/00* (2006.01)

(52) U.S. Cl.
CPC ...... *C12Q 1/6806* (2013.01); *B01L 3/502738* (2013.01); *B01L 3/502761* (2013.01); *B01L 3/502784* (2013.01); *B01L 7/52* (2013.01); *B01L 2200/027* (2013.01); *B01L 2200/141* (2013.01); *B01L 2300/021* (2013.01); *B01L 2400/0424* (2013.01); *B01L 2400/0436* (2013.01); *B01L 2400/0439* (2013.01); *B01L 2400/0487* (2013.01); *B01L 2400/06* (2013.01)

(58) Field of Classification Search
CPC ............ C12Q 1/6806; C12Q 2563/179; B01L 3/502738; B01L 3/502784
See application file for complete search history.

(56) References Cited

U.S. PATENT DOCUMENTS

2013/0225418 A1    8/2013  Watson

FOREIGN PATENT DOCUMENTS

EP          2 805 769 A1     11/2014

OTHER PUBLICATIONS

Zec, Helena et al. "Microfluidic platform for on-demand generation of spatially indexed combinatorial droplets" Lab on a Clip (2012) vol. 12, pp. 3055-3062.
Macosko, Evan Z. et al. "Highly parallel genome-wide expression profiling of individual cells using nanoliter droplets" Cell (2015) vol. 161(5), pp. 1202-1214.
Zeng, Shaojiang et al. "Microvalve-actuated precise control of individual droplets in microfluidic devices" Lab on a Chip (2009) vol. 9, pp. 1340-1343.
Rakszewska, Agata et al. "One drop at a time: toward droplet microfluidics as a versatile tool for single-cell analysis" NPG Asia Material (2014) vol. 6(10), pp. e133.
The International Search Report (ISR) with Written Opinion for PCT/EP2016/064877 dated Jul. 27, 2016, pp. 1-13.

*Primary Examiner* — David C Thomas
(74) *Attorney, Agent, or Firm* — Hamre, Schumann, Mueller & Larson, P.C.

(57) ABSTRACT

The present invention relates to the field of microfluidics and in particular to methods for co-localizing a particle comprising DNA and/or RNA with a known barcode oligonucleotide. Thereby, the transcriptome or DNA of a cell can be barcoded and correlated to a cell phenotype or examined for the effect of a drug on the cell. The invention also provides microfluidic devices and systems having properties which make them particularly suitable for use in the methods of the invention.

14 Claims, 11 Drawing Sheets

A

B

A

B

CELL BARCODING IN MICROFLUIDICS

CROSS-REFERENCE TO RELATED APPLICATION

Figure 1:
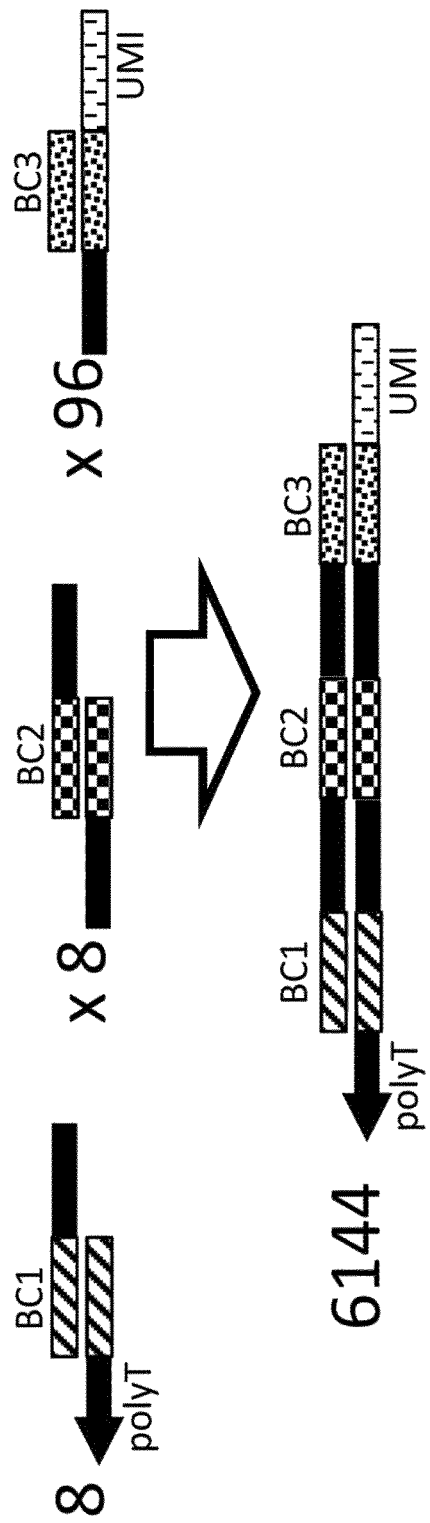
Figure 1:
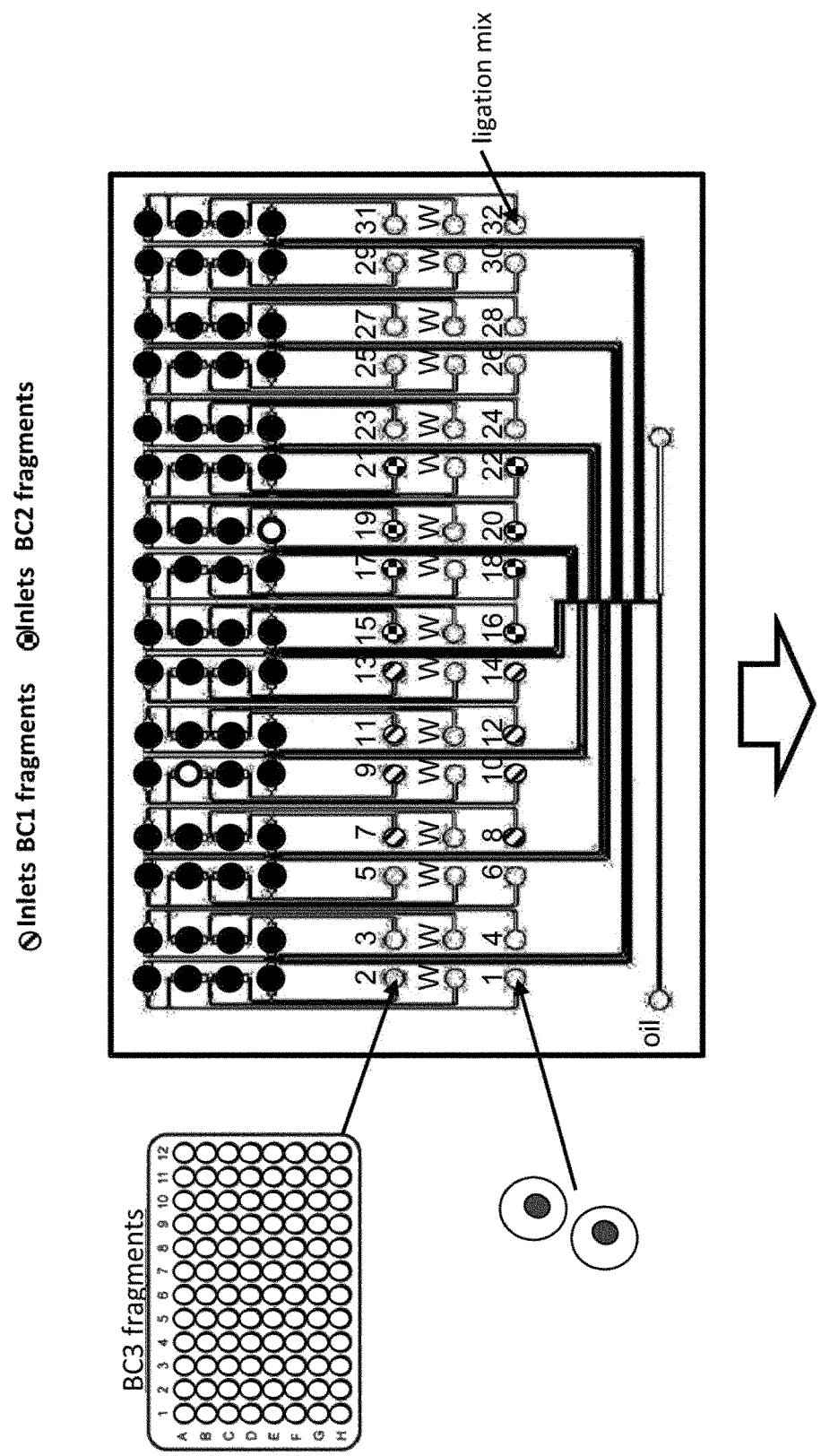
Figure 1:
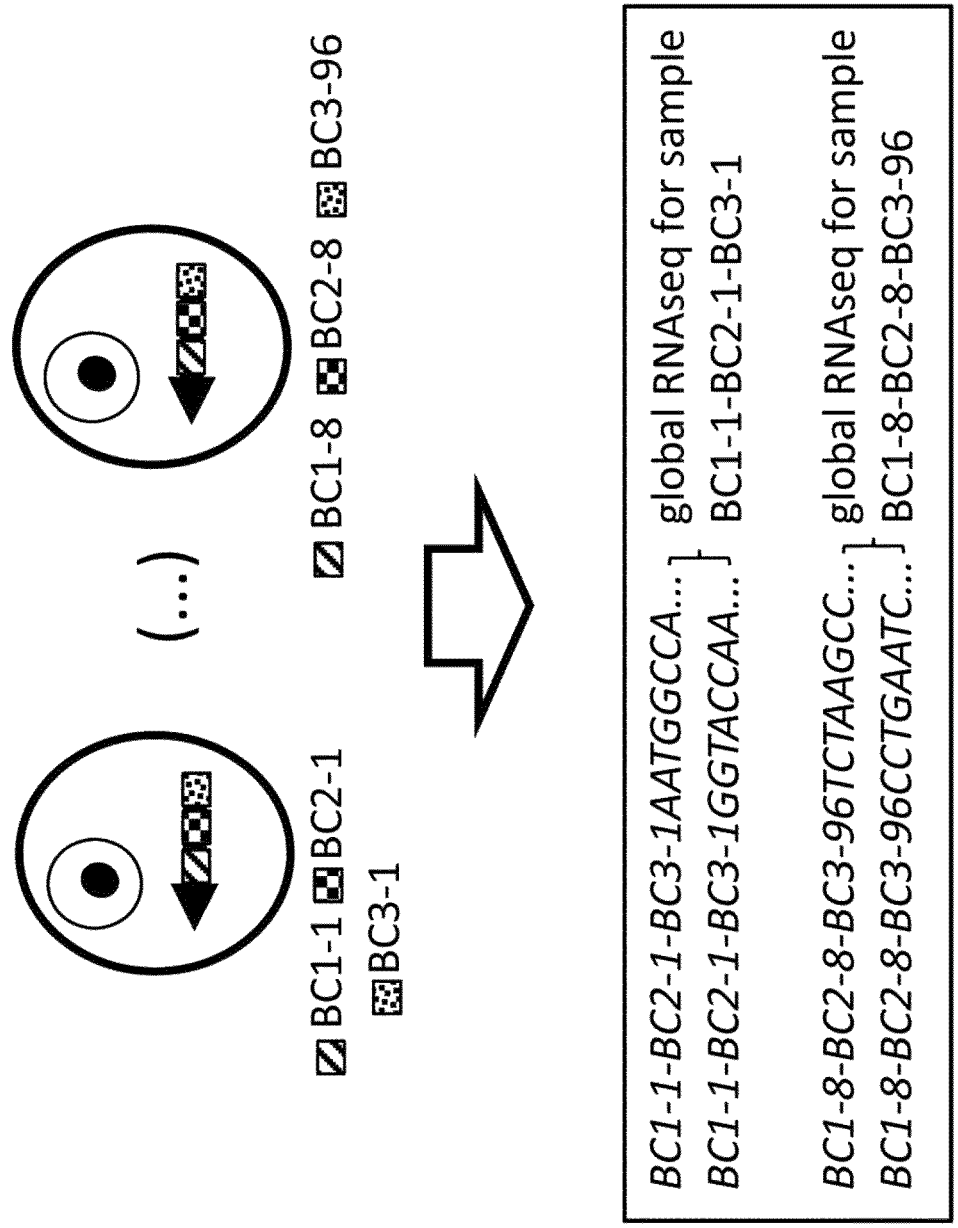

This application is a U.S. national phase of International Application No. PCT/EP2016/064877, filed on Jun. 27, 2016, which claims priority to European Patent Application No. 15174088.3, filed Jun. 26, 2015, both of which are incorporated by reference herein in their entirety.

FIELD OF THE INVENTION

The present invention relates to the field of microfluidics and in particular to methods for co-localizing a particle comprising DNA and/or RNA with a known barcode oligonucleotide. Thereby, the transcriptome or DNA of a cell can be barcoded and correlated to a cell phenotype or examined for the effect of a drug on the cell. The invention also provides microfluidic devices and systems having properties which make them particularly suitable for use in the methods of the invention.

BACKGROUND OF THE INVENTION

The barcoding of cellular mRNAs with unique identifiers, such as incorporation of unique nucleotide sequences during cDNA synthesis, is widely used in genomic applications (A. E. Saliba, A. J. Westermann, S. A. Gorski, J. Vogel, Single-cell RNA-seq: advances and future challenges. *Nucleic Acids Research* 42, 8845 (2014)). For example, it can be exploited in single-cell analysis to clearly assign specific mRNA sequences to individual cells, even when sequencing pooled samples. Furthermore, genetic barcoding is of major use for pharmacogenomics studies, e.g. for analysing the effect of a particular drug on the transcriptome. This approach holds enormous potential in drug screening, since it enables screening drug candidates not only for the effect on one particular drug target, but rather for their effect on global gene expression. In consequence, this helps revealing potential side effects, but as well allows to predict the effect of drug combinations and to establish "precision therapies".

Current high throughput cell barcoding approaches make use of beads or gel particles displaying thousands of copies of the same barcoded polyT primer (H. C. Fan, G. K. Fu, S. P. A. Fodor, Combinatorial labeling of single cells for gene expression cytometry. *Science* 347, 628, Feb. 6, 2015; E. Z. Macosko, A. Basu, R. Satija, J. Nemesh, K. Shekhar, M. Goldman, I. Tirosh, A. R. Bialas, N. Kamitaki, E. M. Martersteck, J. J. Trombetta, D. A. Weitz, J. R. Sanes, A. K. Shalek, A. Regev and S. A. McCarroll, *Cell,* 2015, 161, 1202-1214). Each bead displays a different primer, however their exact barcode sequence is not known since they are synthesized in a combinatorial split-and-pool (solid phase) synthesis. The beads are then incubated with the cell samples (optionally on the single-cell level), and the cellular mRNAs are reverse transcribed into cDNA harbouring the respective barcode sequences. This allows pooling the cells for sequencing their transcriptome, while still being able to distinguish transcriptome patterns from different cells. Nonetheless, a direct coupling of a particular transcriptome pattern with a particular individual cell is impossible.

Overcoming this limitation, the inventors have developed a microfluidic approach enabling to barcode single cells, as well as cell populations. The method is based on the combinatorial assembly of barcoding primers, using valve-based microfluidic technology. In contrast to existing systems (e.g. as sold by Fluidigm), as well as recent publications, for example in Science (H. C. Fan, G. K. Fu, S. P. A. Fodor, Combinatorial labeling of single cells for gene expression cytometry. *Science* 347, 628, Feb. 6, 2015; E. Z. Macosko, A. Basu, R. Satija, J. Nemesh, K. Shekhar, M. Goldman, I. Tirosh, A. R. Bialas, N. Kamitaki, E. M. Martersteck, J. J. Trombetta, D. A. Weitz, J. R. Sanes, A. K. Shalek, A. Regev and S. A. McCarroll, *Cell,* 2015, 161, 1202-1214; A. M. Klein, L. Mazutis, I. Akartuna, N. Tallapragada, A. Veres, V. Li, L. Peshkin, D. A. Weitz and M. W. Kirschner, *Cell,* 2015, 161, 1187-1201), this technology is not making use of degenerated, random barcodes, but rather allows labelling cells with barcodes of known identity. Hence one cannot only distinguish between the transcriptome of different cells, but also correlate a particular transcriptome with a particular phenotype or a sample exposed to a particular drug. This opens the way for manifold new applications.

SUMMARY OF THE INVENTION

In a first aspect, the present invention relates to a method for co-localizing a particle comprising DNA and/or RNA with a known barcode oligonucleotide or set of components thereof in a microfluidic droplet in a microfluidics system, comprising:
(i) feeding a particle comprising DNA and/or RNA into a co-localizing channel,
(ii) passing the particle past a series of at least two valve-operated oligonucleotide inlets or sets of valve-operated oligonucleotide inlets, wherein one of the at least two oligonucleotide inlets or sets of oligonucleotide inlets is open while the particle passes it, and wherein each oligonucleotide inlet, when open, feeds a known barcode oligonucleotide or set of components thereof into the co-localizing channel, or each set of oligonucleotide inlets, when open, feeds a set of components of a known barcode oligonucleotide into the co-localizing channel, and
(iii) closing the oligonucleotide inlet or set of oligonucleotide inlets that is open after the particle has passed it and opening a different oligonucleotide inlet or set of oligonucleotide inlets of the at least two valve-operated oligonucleotide inlets or sets of valve-operated oligonucleotide inlets,
wherein
(A) the particle of step (i) and the known barcode oligonucleotide or the set of components thereof of step (ii) are fed into the co-localizing channel while not comprised in microfluidic droplets, and the method further comprises generating microfluidic droplets downstream of the at least two valve-operated oligonucleotide inlets or sets of oligonucleotide inlets prior, during or after step (iii), including a microfluidic droplet comprising the particle and the known barcode oligonucleotide or components thereof, or
(B) the particle of step (i) and the known barcode oligonucleotide or the set of components thereof of step (ii) are fed into the co-localizing channel comprised in microfluidic droplets and these microfluidic droplets are fused.

In a second aspect, the invention relates to a method for barcoding the transcriptome of a cell, for barcoding a DNA amplificate from a cell or for barcoding the genome of a cell, comprising the steps of
(i) co-localizing a cell with a known barcode oligonucleotide in a microfluidic droplet using the method of the first aspect,
(ii) lysing the cell in the microfluidic droplet, and (iii) annealing the barcode oligonucleotide to RNA or DNA of the lysed cell in the microfluidic droplet, (iv) carrying out a reverse transcription (RT), RT-PCR, PCR, or a transposition reaction using the annealed barcode oligonucleotide as primer(s) or transposable elements, respectively, in the microfluidic droplet or in an aqueous phase in which the microfluidic droplet is disrupted, thereby generating a barcoded transcriptome, DNA amplificate or genome, wherein an RT mix, an RT-PCR mix, a PCR mix, or a transposition mix, respectively, is comprised in the co-localizing channel in step (i), is comprised in a microfluidic droplet fused to the microfluidic droplet of step (i), (ii) or (iii) or is comprised in an aqueous phase in which the microfluidic droplet is disrupted.

In a third aspect, the present invention relates to a method for correlating the phenotype of a single cell with its transcriptome, with a DNA amplificate derived from the cell or with its genome, comprising barcoding the transcriptome of a single cell, barcoding a DNA amplificate from a single cell or barcoding the genome of a single cell using the method of the second aspect, wherein the cell is phenotyped in step (i), and wherein the sequence of the barcode in the barcoded transcriptome, amplificate or genome indicates the phenotype of the cell from which the transcriptome, DNA amplificate or genome is derived.

In a fourth aspect, the present invention relates to a method for determining the effect of a drug on the transcriptome of a cell or on an DNA amplificate from a cell, comprising barcoding a transcriptome of a cell or a DNA amplificate from a cell using the method of the second aspect including steps (v) and (vi) (as described below), wherein the DNA amplificate is generated from mRNA by RT-PCR, wherein a known drug is fed into the microchannel in step (i) of the second aspect, and wherein the sequence of the barcode in the barcoded transcriptome or the barcoded DNA amplificate indicates the drug to which the cell was exposed or the cell which was exposed to the drug.

In a fifth aspect, the present invention relates to a microfluidic device, comprising a microfluidic channel comprising a series of at least two valve-operated aqueous fluid inlets or sets of valve-operated aqueous fluid inlets for feeding an aqueous fluid into the microfluidic channel, an immiscible fluid inlet downstream of the series of at least two aqueous fluid inlets or sets of aqueous fluid inlets for feeding an immiscible fluid into the microfluidic channel to generate microfluidic droplets, (i) a collection channel and a waste channel forming a junction downstream of the microfluidic channel, and a channel selection means; or (ii) a further valve-operated aqueous fluid inlet upstream of the series of at least two valve-operated aqueous fluid inlets or sets of valve-operated aqueous fluid inlets, wherein only one of the at least two valve-operated aqueous fluid inlets or sets of valve-operated aqueous fluid inlets is open at any one time, characterized in that (i) the channel selection means is operatively linked to the valves of the aqueous fluid inlets such that microfluidic droplets comprising what is fed into the microfluidic channel by more than one of the at least two aqueous fluid inlets or sets of aqueous fluid inlets are sent either to the waste or the collection channel, preferably to the waste channel; or (ii) the further valve-operated aqueous fluid inlet is operatively linked to the valves of the aqueous fluid inlets of the series of at least two valve-operated aqueous fluid inlets or sets of valve-operated aqueous fluid inlets such that the further valve-operated aqueous fluid inlet closes to avoid that microfluidic droplets comprising what is fed into the microfluidic channel by more than one of the at least two aqueous fluid inlets or sets of aqueous fluid inlets also comprise what is fed into the microfluidic channel by the further valve-operated aqueous fluid inlet, and then opens.

LEGENDS TO THE FIGURES

FIG. 1: Microfluidic barcoding of cellular mRNAs using soluble primers. A) Primers are assembled from three different fragments, each one including a sequence barcode of, in this example, 4 nucleotides: The first fragment contains a single-stranded polyT stretch (black) and the first double-stranded barcode building block (BC1, striped). It also contains an additional single-stranded overhang (black) to facilitate hybridization with the second fragment. This second fragment contains further single-stranded hybridization sequences, as well as the second double-stranded barcode building block (BC2, checkered). The third fragment looks similar (harbouring barcode building block BC3, dotted), but additionally contains a 5'-unique molecular identifier (UMI, dashed), a sequence that differs in every single copy of this primer (see, e.g., S. Islam et al., Quantitative single-cell RNA-seq with unique molecular identifiers. *Nature methods* 11, 163, February, 2014). Starting with a total of 8 different BC1-fragments, 8 different BC-2 fragments and 96 different BC-3 fragments, a total of 6144 uniquely barcoded RT-primers can be assembled by ligation. B) Microfluidic workflow: Cells, primer fragments and ligation mix are injected into different inlets of the microfluidic chip (shown here is a combinatorial Braille chip) and encapsulated into droplets. The Braille valves (black and open circles in the upper part of the chip) ensure that different primer fragments can be mixed on demand. Inlet 1 is for cells. Inlet 2 is associated with a plate with 96 different BC3 fragments. The 8 lined BC1 inlets 7-14 are for 8 different BC1 fragments and the 8 chequered BC2 inlets 15.22 are for 8 different BC2 fragments. Subsequent to encapsulation (step indicated by the first large arrow), the fragments are ligated. Then (step indicated by the second large arrow), the droplets are fused with a second droplet species hosting RT mix before they are incubated at 50° C. to initiate reverse transcription of cellular mRNAs. In a next step, the droplets are broken and the aqueous contents are pooled. Downstream sequencing finally allows to obtain expression patterns that can be distinguished for different samples.

Figure 2:
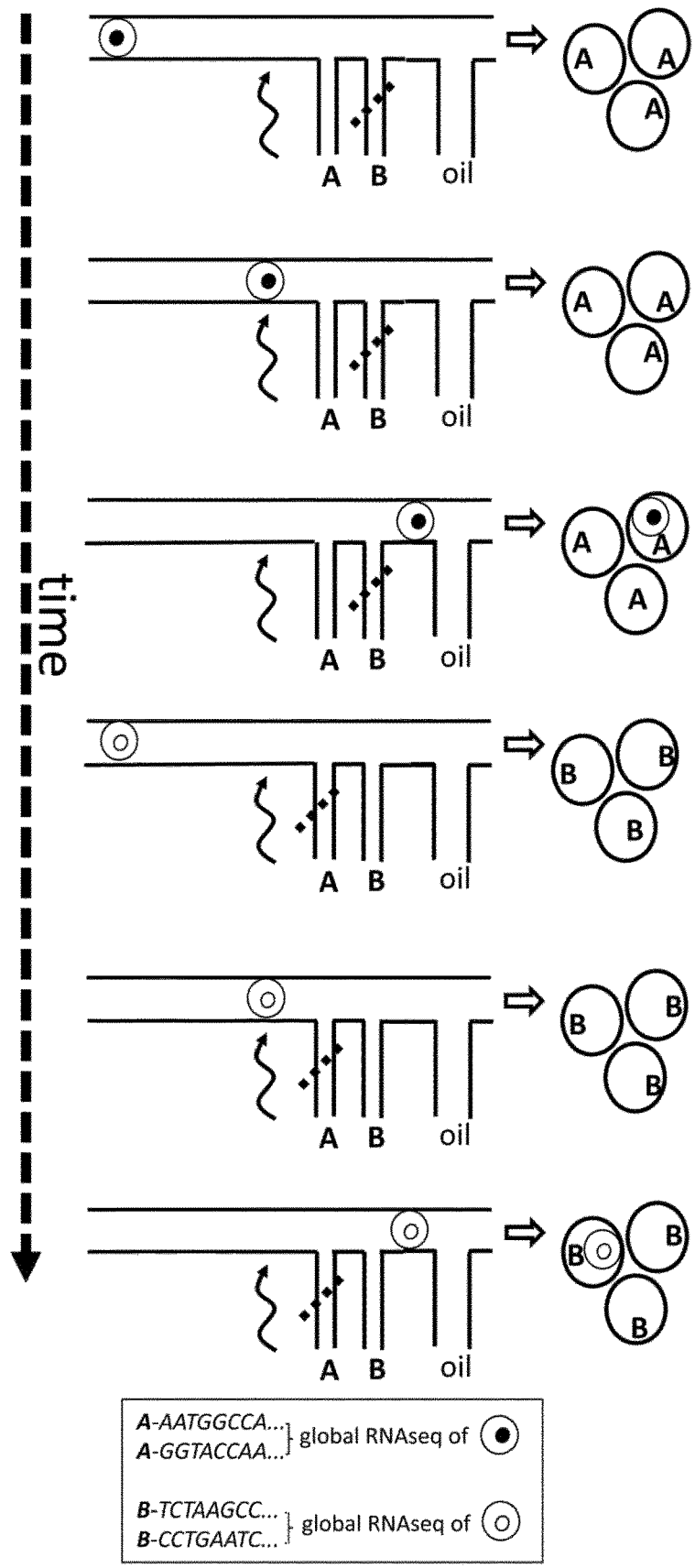

FIG. 2: Phenotype/genotype correlation studies. Droplets hosting a uniquely barcoded poly-T primer (optionally assembled from fragments) of identity A are continuously encapsulated into droplets. Whenever a cell (i) passes the detection point, its phenotype is determined (e.g. by fluorescence spectroscopy as indicated by the waved arrow) before it is encapsulated into a droplet together with primer A. Immediately after this is done, valves are switched so that from now onwards droplets hosting primer B are generated. The phenotype of the next cell (i+1) is determined as before, but this particular cell is now encapsulated with primer B. Final sequence analysis then allows to assign particular expression patterns to the previously determined phenotype (box at the bottom). Dotted lines depict closed valves.

Figure 3:
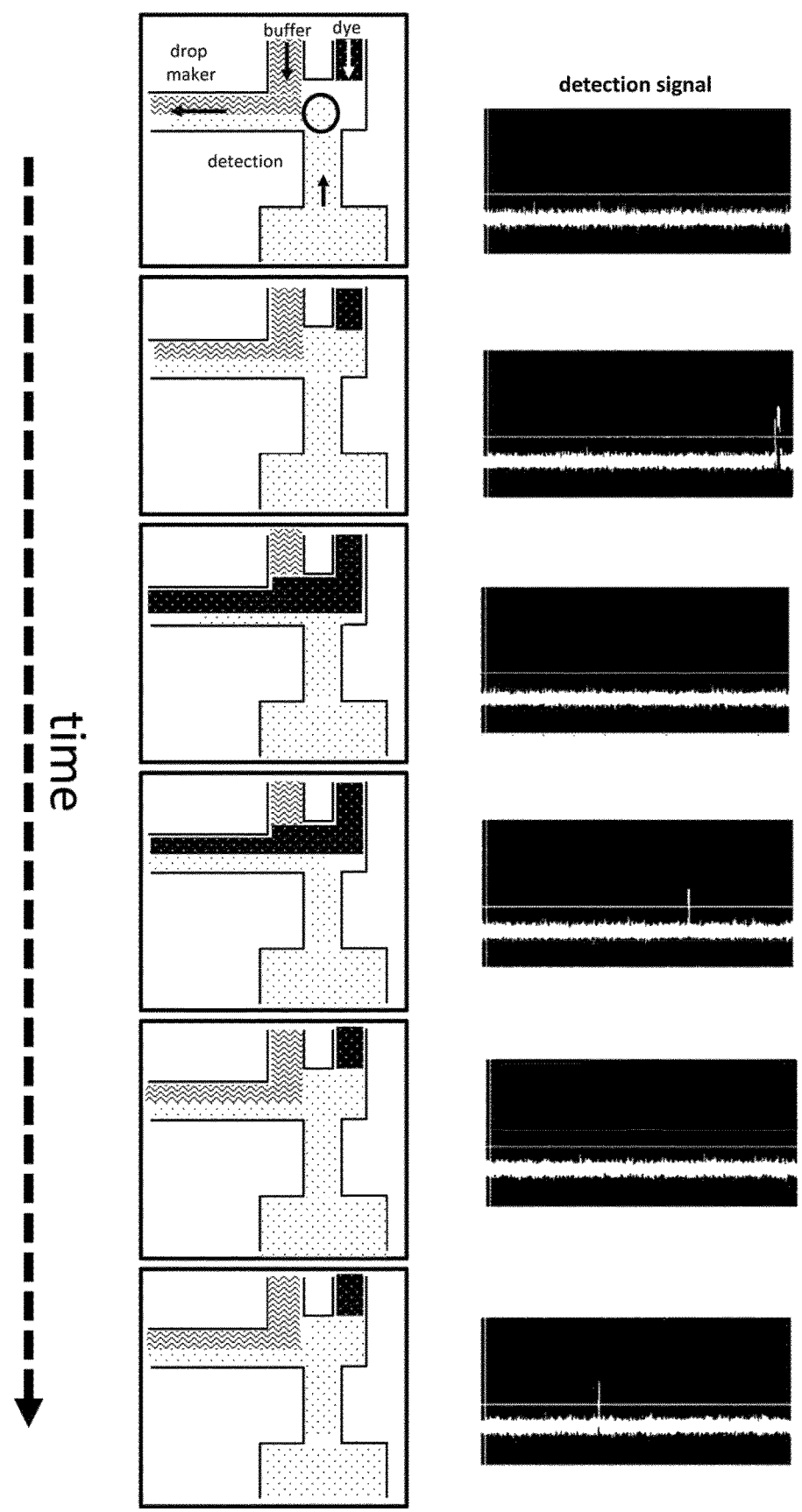

FIG. 3: Switching of microfluidic valves upon detection of a cell. Left panel: cells are analyzed at the detection point (e.g. by laser spectroscopy when using fluorescently labelled cells) and encapsulated with any desired reagent such as buffer. Whenever a cell (i) is detected it is encapsulated together with this reagent, but immediately afterwards the valves are switched so that the next cell (i+1) is encapsulated with another reagent such as dye or any mixture of choice. In this example, the valves were repetitively switched back and forth so that cells are alternatingly co-encapsulated with buffer or dye. Right panel: fluorescence signals of cells passing the detector. Each peak indicates a single cell flowing through the channel. Y-axis shows the signal intensity and X-axis the measurement time course.

Figure 4:
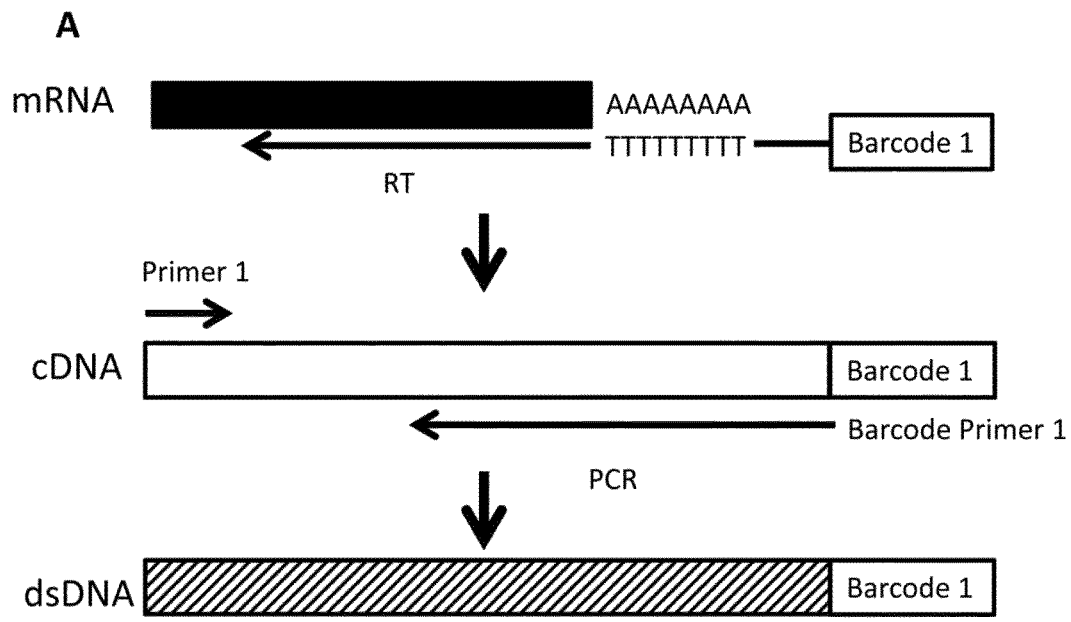
Figure 4:

FIG. 4: Barcoding of cellular mRNA/cDNA in droplets. Cells were encapsulated together with a barcoded primer and RT-mix. Subsequent to incubation at 50° C. to allow for reverse transcription, the droplets were broken and the aqueous contents were pooled. Then the barcoded cDNA was PCR-amplified using a forward primer for particular genes (e.g. MMP-2, GAPDH, MMP-14) and a reverse primer complementary to the newly introduced barcode. This way, only cDNA, but not gDNA (genomic DNA) was amplified, proving the feasibility of the approach. A) RT-PCR strategy. B) Analysis of amplified products on agarose gel.

Figure 5:
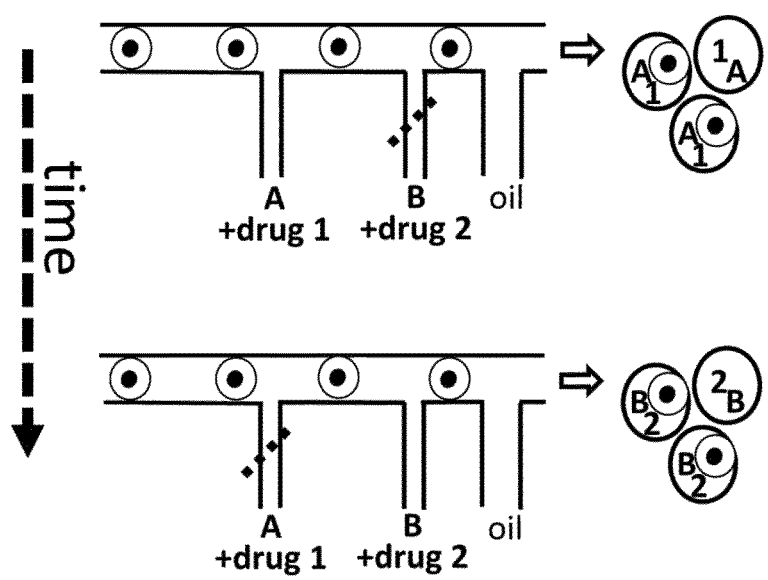

FIG. 5: Pharmacogenomic assays. Cells are encapsulated together with drugs (A,B) or combinations thereof. For each sample composition, a uniquely-labelled polyT-primer (optionally assembled from fragments) is added. After incubation of the droplets (to allow for the drug effect and ligation of primer fragments) the droplets are fused with a second droplet species hosting all reagents for reverse transcription. Subsequent to a further incubation step at 50° C. (sufficiently long to complete RT), the droplets are broken and the aqueous contents are pooled. Downstream sequence analysis then allows to assign particular expression patterns to the effect of particular drugs. Dotted lines depict closed valves.

Figure 6:
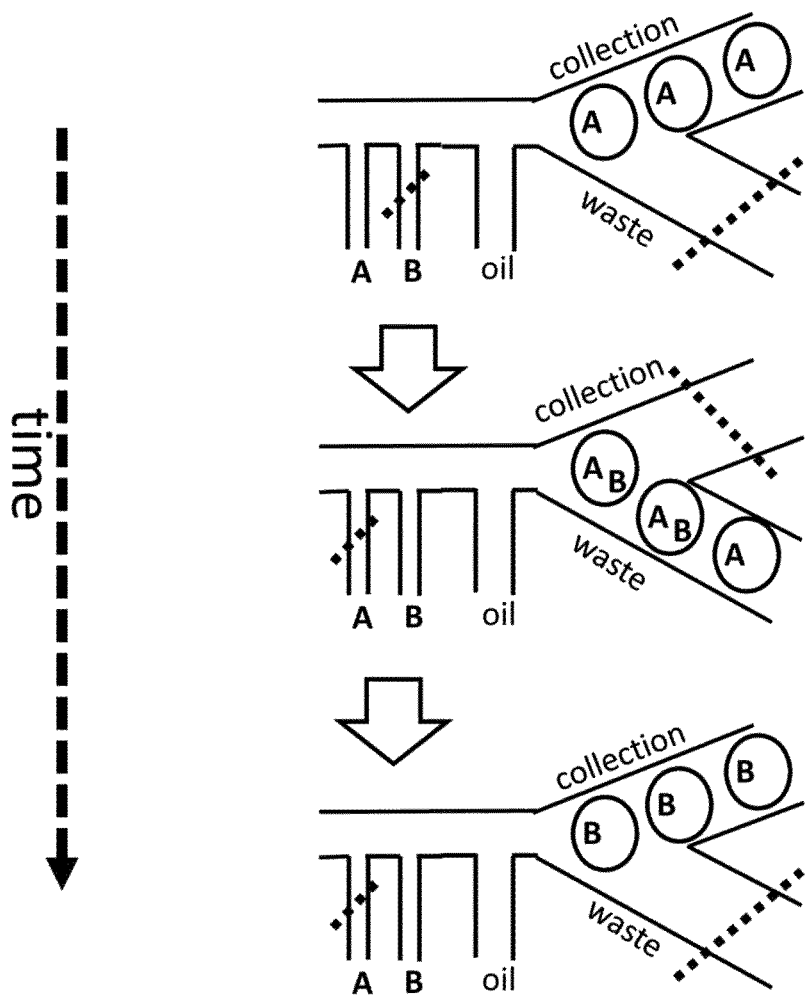

FIG. 6: Strategy for avoiding cross contamination of droplets. The first state (from top to bottom) shows production and collection of droplets hosting A, the second state production of droplets hosting B plus an intermediate step to eliminate cross-contaminated droplets, and the third state a production and collection of droplets hosting B. The arrow between the first and the second state indicates the switching of reagent—and droplet destination valves, and the arrow between the second and the third state the switching of droplet destination valves. Whenever a new droplet composition is generated by switching valves, the very first droplets of this new kind will still contain traces of the previous sample composition. This happens inevitably as the valves are upstream of the merging channels which hence still contain some previous reagents whenever the valves are switched. However, cross-contaminated droplets can be eliminated by having two different channels (collection and waste) downstream of the droplet maker, each one controlled by a valve. Whenever a new sample composition is generated, the very first droplets of this kind (suffering from cross contamination) are sent to the waste, while shortly afterwards the valves are switched and the samples containing the pure, desired composition are collected. Dotted lines indicate closed valves.

Figure 7:
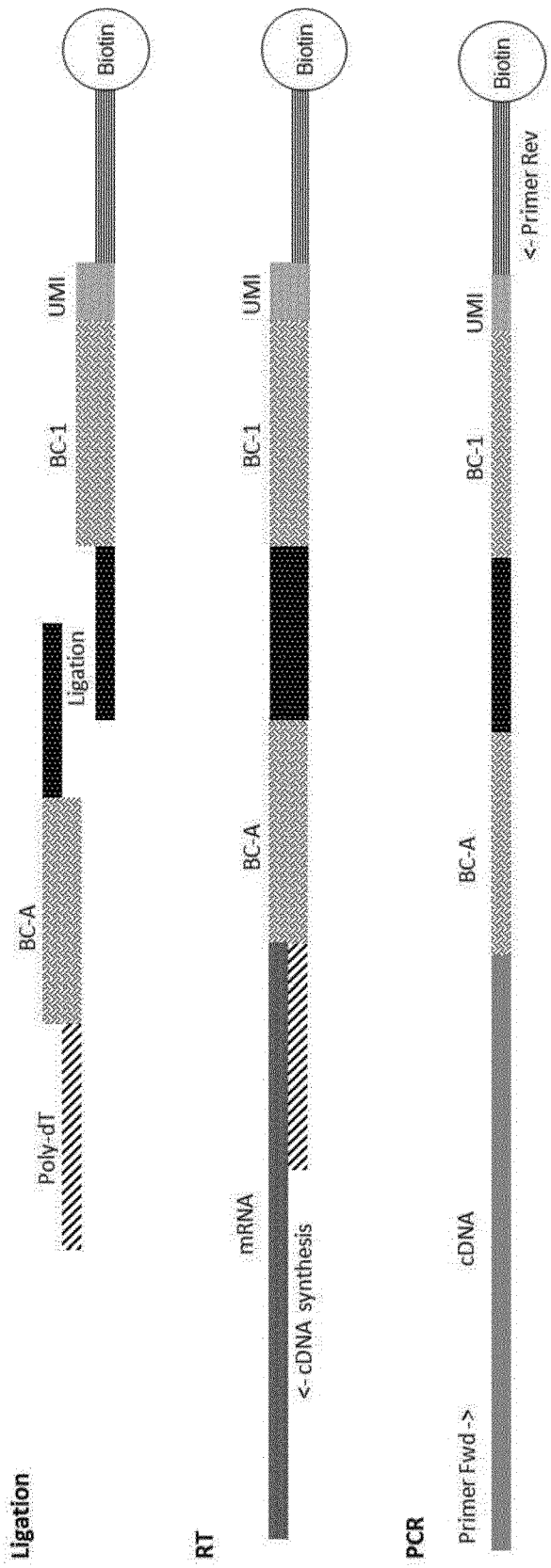

FIG. 7: Generation of barcode combinations. Two barcode fragments with complementary annealing sites (e.g. BC-A and BC-1) are combined in a ligation reaction. One of the combined barcode fragment contains a biotin modification, the other a Poly-dT sequence with a free 3'-OH end. The Poly-dT sequence is used for priming the synthesis of cDNAs from cellular mRNAs in a subsequent reverse transcription (RT) resulting in cDNA sequences labelled with a combination of two barcodes. The cDNAs are purified using streptavidin coated beads and can be amplified by PCR.

Figure 8:
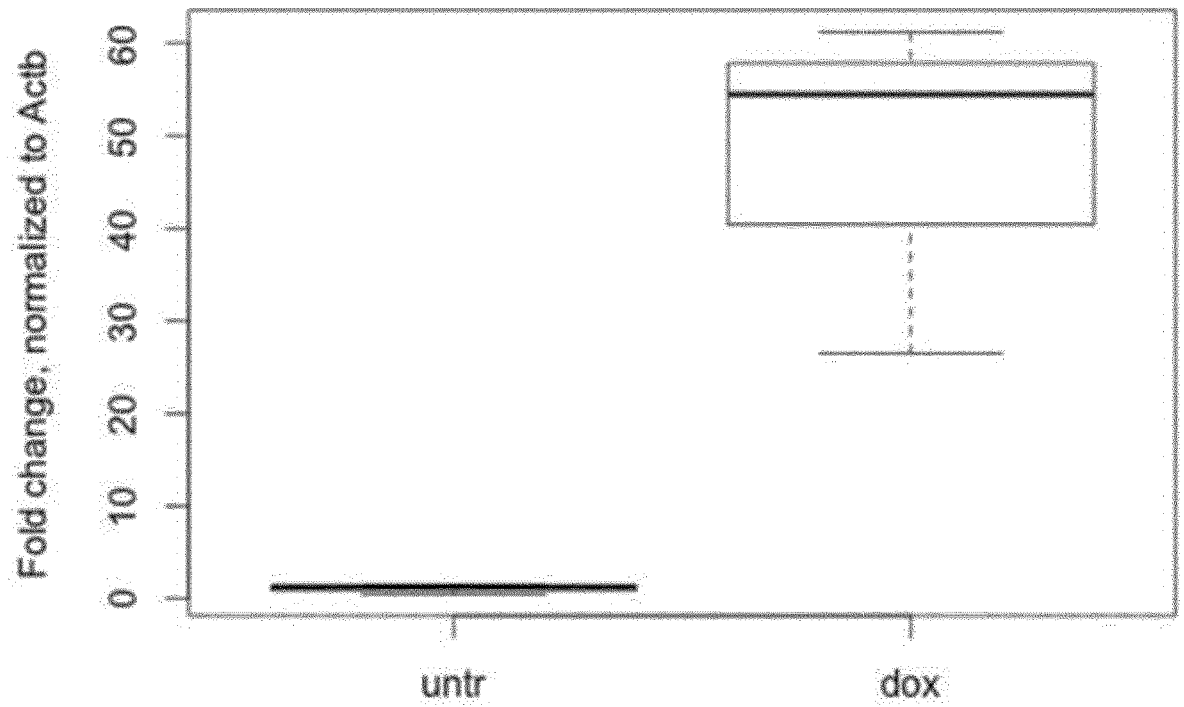
Figure 8:
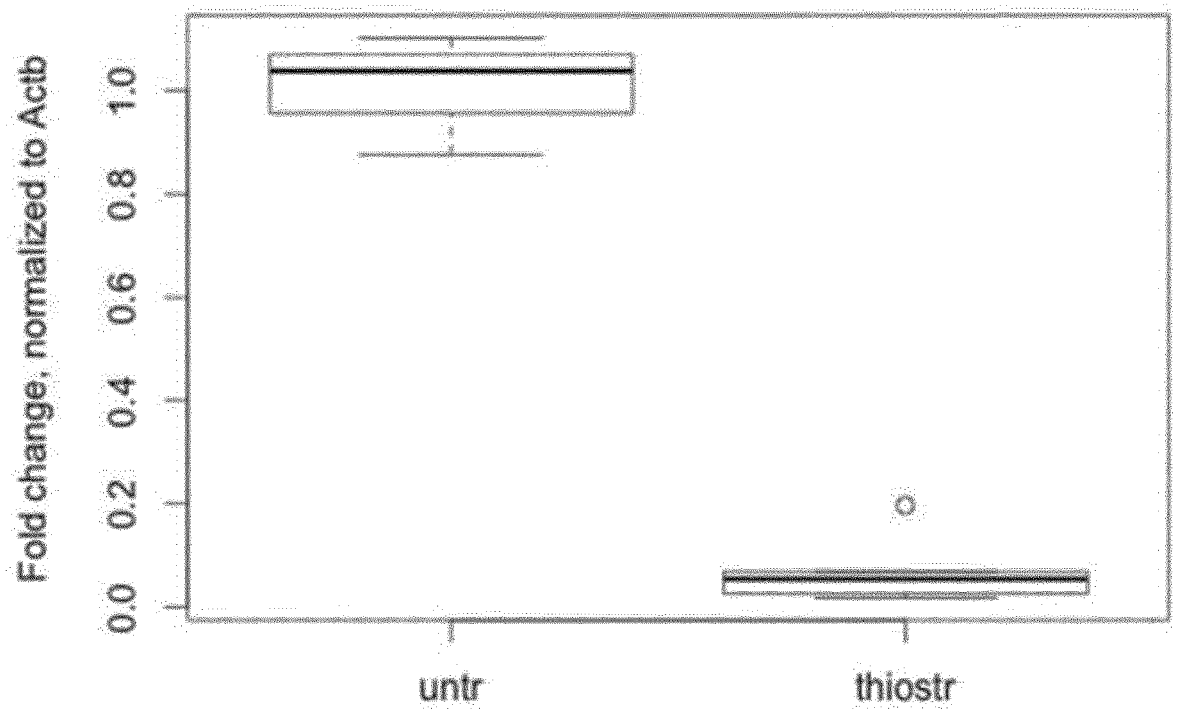

FIG. 8: Expression levels of p21 (A) and FoxM1 (B) normalized to Actb expression. Fold change in expression shown between treated and untreated cells according to Example 5.

Figure 9:
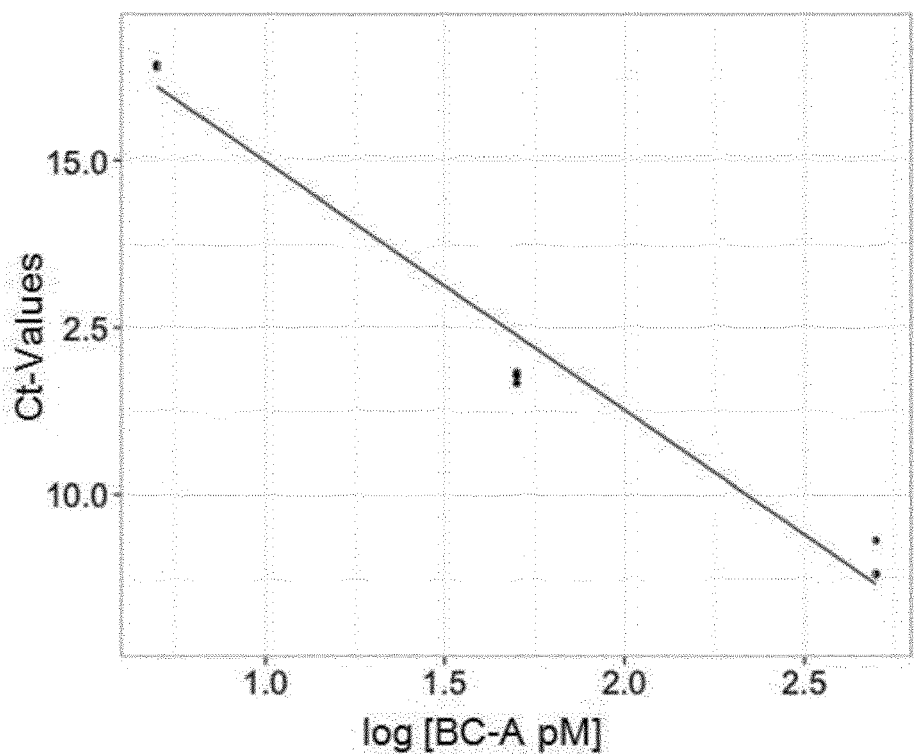
Figure 9:
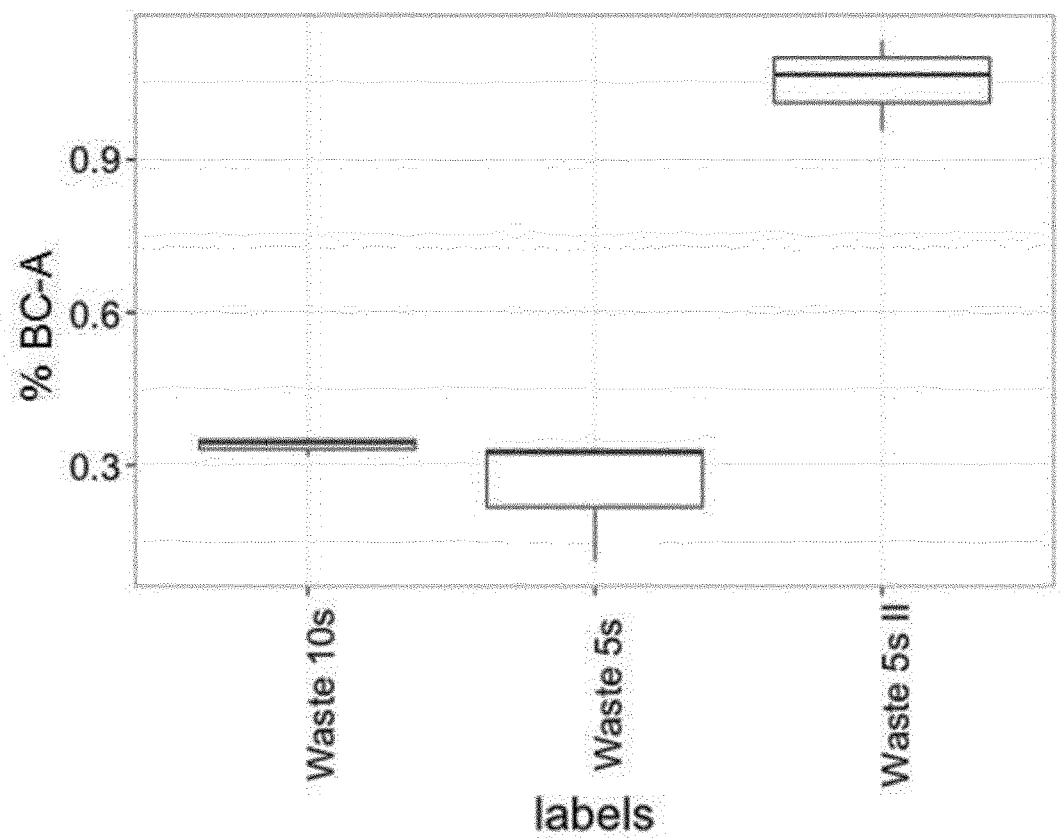

FIG. 9: Cross-contaminations with barcode BC-A using BC-A-specific taqman probes according to Example 6. A: Standard curve prepared using different ratios of BC-A (X-axis) spiked into a BC-C solution. B: Estimated BC-A cross-contamination in the test sample.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland) and in "Encyclopedia of Microfluidics and Nanofluidics", Springer Reference, Volume 1.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In a first aspect, the present invention relates to a method for co-localizing a particle comprising DNA and/or RNA with a known barcode oligonucleotide or set of components thereof in a microfluidic droplet in a microfluidics system, comprising:

(i) feeding a particle comprising DNA and/or RNA into a co-localizing channel,
(ii) passing the particle past a series of at least two valve-operated oligonucleotide inlets or sets of valve-operated oligonucleotide inlets, wherein one of the at least two oligonucleotide inlets or sets of oligonucleotide inlets is open while the particle passes it, and wherein each oligonucleotide inlet, when open, feeds a known barcode oligonucleotide or set of components thereof into the co-localizing channel, or each set of oligonucleotide inlets, when open, feeds a set of components of a known barcode oligonucleotide into the co-localizing channel, and
(iii) closing the oligonucleotide inlet or set of oligonucleotide inlets that is open after the particle has passed it and opening a different oligonucleotide inlet or set of oligonucleotide inlets of the at least two valve-operated oligonucleotide inlets or sets of valve-operated oligonucleotide inlets,
wherein
(A) the particle of step (i) and the known barcode oligonucleotide or the set of components thereof of step (ii) are fed into the co-localizing channel while not comprised in microfluidic droplets, and the method further comprises generating microfludic droplets downstream of the of at least two valve-operated oligonucleotide inlets or sets of oligonucleotide inlets prior, during or after step (iii), including a microfluidic droplet comprising the particle and the known barcode oligonucleotide or components thereof, or
(B) the particle of step (i) and the known barcode oligonucleotide or the set of components thereof of step (ii) are fed into the co-localizing channel comprised in microfluidic droplets and these microfluidic droplets are fused.

The term "co-localizing in a microfluidic droplet" refers basically to putting two or more entities, such as a particle and a barcode oligonucleotide or components thereof, into the same microfluidic droplet. This can be achieved as described below, for example, by generating a microfluidic droplet from an aqueous fluid containing these entities or by fusing droplets separately containing these entities.

The term "microfluidic droplet" refers to an aqueous microcompartment of a certain size that encapsulates an aqueous liquid. The size of the microfluidic droplet can be expressed as the diameter of the droplet. The diameter is generally between 20 and 400 µm, and preferably between 30 and 350 µm, between 40 and 300 µm, between 40 and 250 µm, between 40 and 200 µm or between 40 and 100 µm (wherein each narrower range is preferred to the foregoing broader ranges and "between" includes the values mentioned). Alternatively, the size of the microfluidic droplet can also be defined by volume. For example, it is usually less than 1 microlitre (µl). Preferably, it is less than 500 nanolitres (nl), less than 250, less than 150, less than 100 or less than 50 nl. In a preferred embodiment, it is between 0.05 and 150 nl, preferably between 0.05 and 125 nl, between 0.05 and 100 nl, between 0.05 and 80 nl, or between 0.05 and 4 nl (wherein each narrower range is preferred to the foregoing broader ranges and "between" includes the values mentioned).

The term "particle comprising DNA and/or RNA" refers to any particle, man-made or natural, which incorporates, envelopes, is attached to, consists of or is in any other way associated with DNA and/or RNA. In a preferred embodiment, it is a biological particle, preferably a cell, a non-cellular life form or a DNA and/or RNA carrier. Most preferably it is a cell. The cell can be any prokaryotic or eukaryotic cell. Preferably, it is a eukaryotic cell, e.g. a yeast cell, plant cell or animal cell. Animal cells include insect, nematode, fish and mammalian cells. More preferably it is mammalian cell, e.g. a mouse, rat, monkey or human cell. For example, it can be a random cell of a heterogeneous cell population (e.g. from a tissue) or it can be a specifically selected cell, selected, e.g., by FACS. Also, it can be a cell a from cell line or a homogeneous culture, for example of a primary cell, wherein "primary" means derived directly from a tissue or organism and not manipulated to have altered properties, e.g. to divide indefinitely. Other examples for cells are developing cells, stem cells or cancer cells. Examples of non-cellular life form are viruses, viroids, cosmids, plasmids, phagemids and the like. Examples of DNA and/or RNA carriers are proteins such as histones or ribosomes. Non-biological particles, such as beads, are also envisaged. A "bead" (also termed "microbead") is a uniform polymer particle with a diameter of up to 1 micrometre, preferably of 0.5 to 500 µm, and with a surface to which nucleic acids can bind or be coupled. The beads referred to herein are usually polyethylene or polystyrene beads or beads made of gel matrices.

The term "DNA" refers to any kind of DNA, for example genomic DNA, cDNA or bisulfite-treated DNA in which non-methylated cytosines are converted, more specifically deaminated to uracil. In a preferred embodiment, the DNA comprised by the particle is a DNA genome.

The term "RNA" refers to any kind of RNA, for example mRNA or non-coding RNA such as tRNA and rRNA. In a preferred embodiment, the RNA comprised by the particle is an RNA genome. In another preferred embodiment, it is a collection of mRNA produced from a DNA genome (herein also referred to as "transcriptome"), such as all mRNA of a cell. The term "barcode oligonucleotide" refers to an oligonucleotide having at least one so-called variable regions, the nucleotide sequence of which is unique for this oligonucleotide compared to other barcode oligonucleotides used. In a preferred embodiment, the barcode oligonucleotide has at least two variable regions, the combined nucleotide sequence of which is unique for this oligonucleotide compared to other barcode oligonucleotides used. "Variable" therein means not that the sequence of a particular oligonucleotide can change, but that there are oligonucleotides which are identical in structure and sequence with the exception of the sequence of the variable regions, i.e. the variable regions are different between oligonucleotides that are otherwise identical in structure and sequence. If the barcode oligonucleotide comprises more than one variable region, each of these variable regions is from separate and combinable components, which can be assembled in a combinatorial fashion to create different barcode oligonucleotides. A "component" thus is an oligonucleotide itself, which has one variable region. A "set of components" is a plurality of oligonucleotides which makes up exactly one barcode oligonucleotide (meaning one identity, not one molecule), i.e. it is a complete set of components. The components of one set combine by annealing into a preferably linear barcode oligonucleotide by virtue of their annealing regions, wherein only one linear combination is possible. Thus, within one set of components, the annealing regions are different between the components, but their variable regions can be identical, although they are more likely to be different as well. The structure of the barcode oligonucleotide and of its components is defined in more detail below.

The term "known barcode oligonucleotide or set of components thereof" refers to the fact that the sequence of the barcode oligonucleotide or of the components of the set of components thereof that is co-localized with a given particle comprising DNA and/or RNA or that is fed into the co-localization channel at a particular point of time is known. It is known for example because the valve configuration/valve switching (opening/closing) is predetermined (i.e. a desired barcode oligonucleotide or set of components thereof is chosen by opening the valves of the respective valve-operated inlets) or because the valve configuration/valve switching is random and the random choice is recorded. For predetermined sequences, for example pre-made files with a determined order of valve opening and closings can be executed. Due to the use of known barcode oligonucleotides or sets of components thereof, the combination of barcodes and particles is deterministic rather than random as in the prior art. The active combinatorial mixing is enabled by the new method for co-localizing a particle and chip architecture and the new microfluidic device, both as described herein, which advantageously may comprise sending droplets to a waste or collection channel, or avoid co-localizing barcodes and particles by closing the particle inlet for a time, as described herein. The microfluidic droplets are created, handled and/or controlled in a microfluidic system or device. A "microfluidics system" or "microfluidics device" refers to a technology that is based on the manipulation of continuous liquid flow through microfabricated channels. Actuation of liquid flow is implemented either by external pressure sources, external mechanical pumps, integrated mechanical micropumps, or by combinations of capillary forces and electrokinetic mechanisms. Process monitoring capabilities in continuous-flow systems can be achieved with highly sensitive microfluidic flow sensors based on MEMS technology. Microfluidic systems or devices typically consist of networks of channels of approximately ten to a few hundred micrometers in diameter into which small quantities of reagents can be injected in a specific sequence, mixed and incubated for a specified time. Assays can be highly parallelized by generating independent compartments using valves (pinching off specific regions of the channels) or two-phase microfluidics, in which aqueous droplets surrounded by an immiscible oil phase serve as closed vessels. These approaches enable drastically reduced assay volumes (pico-nanoliters) and strongly improved throughput. For example, droplets can be generated at rates of more than 1,000 per second. Furthermore, microfluidic modules for the splitting, fusion and sorting of droplets at similar rates have been developed, thus providing a repertoire of manipulations mimicking classical bench top procedures.

In a preferred embodiment (applying to all aspects herein), the device, in particular the channels, is/are large enough to handle droplets comprising eukaryotic cells. In other words, the device, in particular the channels, is/are large enough to handle droplets of the sizes described herein, in particular 100 μm diameter droplets.

In the most preferred embodiment, the microfluidics system or device is a Braille pin based microfluidics system or device (i.e. a system comprising Braille pin pinch microvalves) or a pneumatic Quake valve based microfluidics system or device (i.e. a system comprising pneumatic Quake microvalves).

The phrase "feeding a particle into a co-localizing channel" refers to delivering a particle into a co-localizing channel from any source and by any means, e.g. from a different microfluidic channel by the modified or unmodified system flow, from an internal or external particle source or reservoir by a syringe or pump etc. Before, during or after feeding, the particle or the flow can be manipulated to create a minimum or otherwise defined distance of the particle to a previous and/or a following particle fed into the co-localizing channel. For instance, the distance can be defined to be in synchrony with the opening and/or closing of the valve-operated oligonucleotide inlets, e.g. such that only one particle passes the series of valve-operated oligonucleotide inlets while the same oligonucleotide inlet or set of oligonucleotide inlets is open and the next particle passes while the next oligonucleotide inlet or set of oligonucleotide inlets is open. Means for such a spacing of particle in microfluidics systems are known in the art and include, for example additional controllable fluid inlets to increase or decrease flow speed depending on direction, dielectrophoretic (DEP) force to manipulate (e.g. slow down, hold or speed up particles) etc.

The term "co-localizing channel" refers to a microfluidic channel. The term "microfluidic channel" can mean a recess or cavity formed in a material by imparting a pattern into a material or by any suitable material removing technique, or can mean a recess or cavity in combination with any suitable fluid-conducting structure mounted in the recess or cavity, such as a tube, capillary, or the like. Generally, it refers to a microchannel of a diameter of 3000 μm or less, 2000 μm or less, 1000 μm or less, preferably 900, 800, 700, 600, 500, 400, 300, 200, 150, 100, 50 μm or less, preferably the diameter is between 20 μm and 3000 μm, preferably between 20 μm and 1000 μm and more preferably between 20 μm and 500 μm or between 20 μm and 100 μm. In a preferred embodiment, the channel is part of a microfluidics network or system. If the channel does not have a circular cross-section, the height and/or width of the channel is/are according to the sizes given for the diameter above. Several types of channels are mentioned herein, such as a co-localizing channel, an oligonucleotide combination channel, an oligonucleotide channel, a collection channel and a waste channel. These are all microfluidic channels as described above. The different terms are merely functional designations serving a clearer description and they do not intend to describe any structural differences of the channels.

The phrase "passing a particle" usually refers to a passive flow of the particle.

The term "series of at least two valve-operated oligonucleotide inlets or sets of valve-operated oligonucleotide inlets" (also referred to herein as "series of oligonucleotide inlets") refers to all inlets through which barcode oligonucleotides or components thereof are fed into the co-localizing channel ("oligonucleotide inlets"). These inlets do not necessarily have to be arranged in a strictly serial fashion along the channel and it is envisaged that more than one inlet can be located at a certain point along the channel, wherein the position in the channel wall differs (e.g. two inlets can be opposite each other or two or more inlets can be distributed along the channel circumference). In as far as the term refers to a "series of at least two valve-operated oligonucleotide inlets" (which may also be referred to as "series of at least two valve-operated barcode inlets"), each oligonucleotide inlet feeds a barcode oligonucleotide or a set of its components into the co-localizing channel. In this case, the barcode oligonucleotide is assembled or the set of components is brought together upstream of the oligonucleotide inlet. In as far as the term refers to a "series of at least two sets of valve-operated oligonucleotide inlets" (which may also be referred to as "series of at least two sets of valve-operated barcode inlets"), which is the preferred alternative, each oligonucleotide inlet of the set feeds only one component of the set of barcode oligonucleotide components into the co-localizing channel, and the set of oligonucleotide inlets feeds the set of barcode oligonucleotide components into the co-localizing channel (i.e. each inlet feeds a different component such that one set of inlets corresponds to one set of components). Importantly, the composition of a set of oligonucleotide inlets can vary as the components of the barcode oligonucleotide can vary. Both alternatives are described in more detail below.

The term "valve-operated" means that an inlet can be closed or opened using a valve. A "valve" or "microvalve" generally relates to a valve which, with respect to fluids, can selectively be brought into one of two distinct states: a valve open state in which fluid can pass through the valve and a valve closed state in which fluid is blocked to pass the valve. Microvalves control routing, timing, and separation of fluids within a microfluidic device. Generally, microvalves can be actuated mechanically, pneumatically, electrokinetically, by phase changes, or by introduction of external force. Accordingly, the microvalves can be independently selected (i.e. the device may contain different microvalves) from the group consisting of electrokinetic microvalves, pneumatic microvalves, pinch microvalves, phase change microvalves, burst microvalves and Braille pin pinch microvalves. Electrokinetic microvalves operate in continuous flow systems, serving as a fluid router that uses electroosmotic flow to switch fluids from one channel to another. Pneumatic microvalves typically rely on a flexible membrane to control the flow pattern in the flow channel. Preferred pneumatic microvalves are pneumatic Quake microvalves. The Quake valve principle involves a bilayer chip, preferably a bilyer PDMS chip with liquid flowing inside the bottom layer while the upper layer integrates an air network. When activated, the latter one can selectively compress and clog channels of the fluidic layer, which enables fluid motion's control (see, e.g. Microfluidic large-scale integration. Thorsen T, Maerkl S J, Quake S R. Science. 2002 Oct. 18; 298(5593):580-4). Pinch microvalves operate by physically deforming the device material, e.g. PDMS, using mechanical pressure. Phase-change microvalves alternate between different phases of materials such as paraffin, hydrogels, or aqueous solutions to modulate flow. Burst microvalves are single-use valves that are opened when a flow resistance is overcome or when a sacrificial membrane is disintegrated. Lastly, Braille pin pinch microvalves generate localized pressure via the mechanical pins of Braille displays, which are normally used to communicate with the blind and represent an inexpensive and easily programmable valve control method. The pinching points may but do not need to be the valving points. In case of the latter, each pin presses onto a liquid-filled reservoir, which acts as a "piston" that transmits the pressure to a membrane-based pneumatic valve. Preferably, the microvalves are Braille pin pinch microvalves or pneumatic Quake microvalves.

The phrase "one of the at least two oligonucleotide inlets or sets of oligonucleotide inlets is open while the sample passes it" refers to the respective valves being open, such that oligonucleotides can be fed into the co-localizing channel through the open inlet(s). "Closing the oligonucleotide inlet or set of oligonucleotide inlets" refers to the closing of the valves such that oligonucleotides cannot be fed into the co-localizing channel through the inlet(s). The closing of the valves preferably occurs before a further particle arrives at the (first inlet of the) series of oligonucleotide inlets. Also, a different oligonucleotide inlet or set of oligonucleotide inlets of the at least two valve-operated oligonucleotide inlets or sets of valve-operated oligonucleotide inlets opens after the particle has passed the series of open inlets and preferably before a further particle arrives at the (first inlet of the) series of oligonucleotide inlets. This is useful in particular if a single particle, e.g. a single cell, is to be co-localized with a barcode oligonucleotide of components thereof. The phrase "after the particle has passed it" (the oligonucleotide inlet or set of oligonucleotide inlets that is open) includes anytime after. Preferably, it can mean immediately after the particle has passed it, just before generating a microfluidic droplet than comprises said particle or at a time between those two events. This is describing the event/timing, but does not necessarily mean that the passing of the particle controls the closing and opening. While this may be the case (e.g. by using detection means linked to and/or controlling the valves), the control may also be by simple timing, for example taking into account the flow speed of the particle (or of the fluid in the channel(s)), the time of feeding into the microfluidic device, the co-localizing channel or the time of passing a detection point or means as well as the distance to travel. It may also be based on particle density in the channel, wherein the timing is estimated. See also below.

In an embodiment in which potentially a plurality of particles (e.g. cells), i.e. one or more particles, is examined, particles are fed into the co-localizing channel at a higher density such that several particles can be co-localized with the known barcode oligonucleotide in the same microfluidic droplet. In this embodiment, the valves of the valve-operated oligonucleotide inlets open and close independent on whether a particle is passing or has passed the series of oligonucleotide inlets. Instead, they open and close in a time-dependent manner.

In a particular embodiment, the closing of inlets and opening of different inlets occurs at the same time. It is important to note that if a set of oligonucleotide inlets is closed and a different set is of oligonucleotide inlets is opened, these two sets may share one or more, but not all oligonucleotide inlets. This is because the sets of oligonucleotide inlets are, as sets of barcode oligonucleotide components, not constant, but are composed of varying members. If a set of oligonucleotide inlets to be closed and a different set of oligonucleotide inlets to be opened share at least one oligonucleotide inlet, the shared oligonucleotide inlet(s) may be closed and open again or may stay open The valves and their opening and closing according to step (ii) can be controlled, for example, by time and/or by one or more particle detection means. Control by time can be based on the time point the particle is fed into the co-localizing channel, the distance it needs to travel to arrive at and leave the series of oligonucleotide inlets as well as the flow speed of the particle. If potentially a plurality of particles is co-localized with the known barcode oligonucleotide in the same microfluidic droplet, the control by time can be arbitrary or based on the frequency or density of the particle in the co-localizing channel. Detections means can be placed, for example, at the start and/or at the end of series of oligonucleotide inlets and trigger the opening and closing of the valves upon detecting a particle. A combination of the two is also possible if the one or more particle detection means are placed at a distance to the start and/or to the end of series of oligonucleotide inlets. In such a case, the control can be based on the time the particle is detected, the distance it needs to travel to arrive at and leave the series of oligonucleotide inlets as well as the flow speed of the particle. Detection means for detecting particles in a microfluidic channel are well known in the art and include light sensors, for example photomultiplier tubes, CMOS or CCD cameras, or detection electrodes. Generally, the detection means is suitable for detecting a particle and/or a label attached to the particle, in particular a fluorescent label, and may use fluorescence or laser spectroscopy, imaging, impedance or magnetic measurements for detection.

In a particularly preferred embodiment, the detection means is within −10 mm to 50 mm, preferably within −1 mm to 30 mm and more preferably within −200 μm to 500 μm of the last inlet of the series of oligonucleotide inlets (wherein a negative value refers to the distance upstream and a positive value to the distance downstream). Most preferably, it is substantially at or up to μm 500 downstream of the series of oligonucleotide inlets, wherein "substantially at" preferably means "at ±200 μm". Also, the detection of a particle triggers, preferably immediately, the closing and opening of the valves as described. Another embodiment is also included, wherein the detection means is downstream of where microfluidic droplets are generated, i.e. downstream of a droplet generator, preferably downstream of the immiscible fluid inlet (see below), preferably within 10,000 μm, more preferably within 5,000 μm, and the detection of a microfluidic droplet comprising a particle triggers, preferably immediately, the closing and opening of the valves as described.

The term "immiscible fluid" refers to a fluid immiscible with the fluid the particle and the barcode oligonucleotide or components thereof are comprised in the co-localizing channel. The immiscible liquid is preferably a hydrophobic liquid, preferably an oil. The oil phase should have a viscosity that is close to that of water and/or be inert with respect to the biological reagents contained in them. Several oils can be used. Low-viscosity silicone oils swell. Polydimethylsiloxane, also called PDMS or dimethicone. PDMS is a polymer widely used for the manufacture of microfluidic chips, and it is a mineral-organic polymer (a structure containing carbon and silicon of the siloxane family), which can change the cross-sectional dimensions of microfluidic channels and influencing the flow properties of microfluidic devices if swelling occurs. Silicone oils can also be used in microfluidic devices fabricated in glass, which are impermeable to these oils. High-viscosity silicone oils can be used in PDMS devices with minimal swelling at the expense of significantly increasing the pressures required to pump them through the microchannels. Hydrocarbon oils can also be obtained in a range of viscosities and have the benefit that there are a large number of commercially available surfactants for them that can stabilize aqueous-in-oil emulsions. However, they also swell PDMS and tend to exhibit poor retention of encapsulated organic reagents, which are often partially soluble in these oils. The preferred oils for use in the methods of the invention are fluorocarbon oils (or flourinated oils), because even low-viscosity versions of these oils do not swell PDMS. In addition, they tend to exhibit excellent retention of reagents in the drops and have high solubility for gases, allowing oxygen and carbon dioxide to passively diffuse in and out of the microcompartments, for unperturbed cellular respiration. This allows cells to survive in fluorocarbon oil emulsions for hours after encapsulation. A disadvantage of fluorocarbon oils, however, is that, due to their much lower prevalence compared with silicone and hydrocarbon oils, there are fewer commercially available surfactants for stabilizing aqueous-in-fluorocarbon emulsions. Surfactants are useful for reducing the surface tension of the oil-water interface and minimizing droplet coalescence. The choice of which surfactant to use is also important for limiting the transfer of reagents between microcompartments. A comprehensive review of surfactants for droplet-based microfluidics is given in Baret (2012 *Lab Chip* 12, 422). The surfactants utilized in droplet-based microfluidics normally consist of a hydrophilic head group and hydrophobic tail. The amphiphilic character of these molecules allows them to assemble at the oil-water interface of the droplet, thereby lowering its interfacial tension and enhancing stability. The chemical properties of the head group of the surfactant impact the biocompatibility of the droplet interface. Surfactants with non-ionic head groups are preferred, as they minimize the adsorption of macromolecules such as proteins and DNA to the droplet interface, minimally impacting the methods of the invention. Suitable fluorosurfactants that can be readily synthesized in the lab are known in the art and described, e.g., in Clausell-Tormos J et al 2008 *Chem. Biol.* 15, 427-37 or Sadtler et al. 1996 *Angew. Chem. Int. Edn Engl.* 35, 1976-8, and many are commercially available, e.g. from Sphere Fluidics Limited, UK. Additives to the aqueous phase can also enhance biocompatibility by increasing the retention of small molecules in the droplets and minimizing adsorption at the oil-water interface. Different oils can be mixed to optimize the properties of the emulsion for a particular application and methods for easily characterizing the properties of the combination that has been selected are known in the art (Kaltenbach et al. 2012 *Lab Chip* 12, 4185).

The term "to generate microfluidic droplets" refers to creating a stream of monodispersed droplets in an immiscible phase. This can be achieved by means of a droplet generator. Microfluidic droplet generators work by combining two or more streams of immiscible fluids and generating a shear force on the discontinuous phase causing it to break up into discrete droplets. Preferred droplet generators are focused-flow droplet generators and T-shaped droplet generators. Focused-flow droplet generators are based on a continuous phase fluid (focusing or sheath fluid) flanking or surrounding the dispersed phase (focused or core fluid), so as to give rise to droplet break-off in the vicinity of an orifice through which both fluids are extruded. T-shaped droplet generators use a microchannel T-junction, at which droplets are spontaneously formed at the intersection, taking advantage of the interface instability between oil and aqueous streams each coming from one direction towards the junction. A wide variety of such compartmentalisation or microencapsulation procedures are available (Benita, S., Ed. (1996). Microencapsulation: methods and industrial applications.

Drugs and pharmaceutical sciences. Edited by Swarbrick, J. New York: Marcel Dekker) and may be used to create the microfluidic droplet used in accordance with the present invention. Indeed, more than 200 microencapsulation or compartmentalisation methods have been identified in the literature (Finch, C. A. (1993) Encapsulation and controlled release. *Spec. Publ.-R. Soc. Chem.* 138, 35). These include membrane enveloped aqueous vesicles such as lipid vesicles (liposomes) (New, R. R. C., Ed. (1990). Liposomes: a practical approach. The practical approach series. Edited by Rickwood, D. & Hames, B. D. Oxford: Oxford University Press) and non-ionic surfactant vesicles (van Hal, D. A., Bouwstra, J. A. & Junginger, H. E. (1996). Nonionic surfactant vesicles containing estradiol for topical application. In *Microencapsulation: methods and industrial applications* (Benita, S., ed.), pp. 329-347. Marcel Dekker, New York.). Preferably, the microfluidic droplets or microcompartments of the present invention are formed from emulsions; heterogeneous systems of two immiscible liquid phases with one of the phases dispersed in the other as droplets of microscopic size (Becher, P. (1957) Emulsions: theory and practice. Reinhold, New York; Sherman, P. (1968) Emulsion science. Academic Press, London; Lissant, K. J., ed Emulsions and emulsion technology. Surfactant Science New York: Marcel Dekker, 1974; Lissant, K. J., ed. Emulsions and emulsion technology. Surfactant Science New York: Marcel Dekker, 1984). Emulsions may be produced from any suitable combination of immiscible liquids. Preferably the emulsion of the present invention has water (containing a particle and other components) as the phase present in the form of droplets and a hydrophobic, immiscible liquid (preferably an oil) as the surrounding matrix in which these droplets are suspended. Such emulsions are termed 'water-in-oil'. This has the advantage that the aqueous phase is compartmentalised in discrete droplets. The external phase, preferably being a hydrophobic oil, generally is inert. The emulsion may be stabilized by addition of one or more surface-active agents (surfactants). These surfactants act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash, M. and Ash, I. (1993) Handbook of industrial surfactants. Gower, Aldershot). Suitable oils are listed above.

In a preferred embodiment of (A), the particle of step (i) and the known barcode oligonucleotide or the set of components thereof of step (ii) are fed into the co-localizing channel while not comprised in microfluidic droplets, and the method further comprises passing the particle past an immiscible fluid inlet downstream of the series of at least two valve-operated oligonucleotide inlets or sets of oligonucleotide inlets prior, during or after step (iii), wherein the immiscible fluid inlet feeds an immiscible fluid into the co-localizing channel to generate microfluidic droplets, including a microfluidic droplet comprising the particle and the known molecular barcode. This embodiment relates to the use of a T-shaped droplet generator.

"Fusing" two droplets results in one microfluidic droplet comprising the contents of the two origin droplets. Thus, the droplet resulting from fusion comprises the contents of the microfluidic droplet comprising the particle and the microfluidic droplet(s) comprising the barcode oligonucleotide or components thereof. One-to-one fusion can be achieved, e.g., according to Mazutis et al. (A fast and efficient microfluidic system for highly selective one-to-one droplet fusion. Lab Chip (2009) vol. 9 (18) pp. 2665-2672). If one-to-one fusion is applied and more than two droplets are fused, the droplet comprising the particle is fused sequentially to the droplets containing the components of the barcode oligonucleotide. Further droplet fusion methods are described in P. Day et al. (eds.), Microdroplet Technology: Principles and Emerging Applications in Biology and Chemistry, Integrated Analytical Systems, DOI 10.1007/978-1-4614-3265-4_2, # Springer Science+Business Media, LLC 2012, Chapter 2.

In a preferred embodiment, the method of the first aspect comprises repeating all steps one or more times with a further particle after step (i) is carried out for the particle fed into the co-localizing channel prior to this further particle, wherein for each particle passing the series of at least two valve-operated oligonucleotide inlets or sets of valve-operated oligonucleotide inlets in step (ii), a different valve-operated oligonucleotide inlet or set of valve-operated oligonucleotide inlets is open, and wherein the barcode oligonucleotide or set of components thereof fed into the co-localizing channel while the particle passes the series is recorded.

This is in particular for the embodiment in which a single particle is co-localized with a barcode oligonucleotide or components thereof. In an embodiment in which potentially a plurality of particles is co-localized with a barcode oligonucleotide or components thereof, as described above, a preferred embodiment comprises repeating all steps one or more times while particles are constantly fed into the co-localizing channel, wherein different valve-operated oligonucleotide inlet or set of valve-operated oligonucleotide inlets open in a time-dependent manner, and wherein the order of the barcode oligonucleotide or set of components thereof fed into the co-localizing channel is recorded.

The term "is recorded" means that it is already on record, i.e. predetermined (see above), or put on record when carrying out the method. The putting on record of the barcode oligonucleotide components feeding can be achieved by recording which valve-operated oligonucleotide inlet or set of valve-operated oligonucleotide inlets is open when particles pass them or at any one time or by recording which valve-operated oligonucleotide inlet or set of valve-operated oligonucleotide inlets is open at any one time over time if a potential plurality of particles is co-localized with a barcode oligonucleotide as described above. Importantly, regarding the former, in this embodiment not all steps have to be completed for one particle before step (i) is carried out for a further particle. Nevertheless, step (i) for a particle must be carried out such that it does not arrive at the series of oligonucleotide inlets before the previous particle has passed this series. In other words, the particles must be spaced such that not more than one particle is within the channel section starting at the first oligonucleotide inlet and ending at the last oligonucleotide inlet of the series of nucleotide inlets at the same time.

In one embodiment, the method of the first aspect further comprises detecting the particle at a detection point in the co-localizing channel. The detection point can be upstream, downstream of even within the series of oligonucleotide inlets. In a preferred embodiment, the detection comprises a characterization of the particle with respect to one or more properties. For example, in an embodiment in which the particle is a cell, the cell is phenotyped at the detection point. This may comprise the detection of any biophysical or biochemical property of the cell, such as size, shape, morphology, staining, for example immunostaining, ligand binding etc. Such a detection, characterization and/or phenotyping can be achieved by imaging techniques, for example bright field or fluorescence imaging, spectroscopy including fluorescence spectroscopy etc. This allows, for instance, to correlate a certain cell phenotype, in particular of a single cell, with its transcriptome or a genetic aberration such as a mutation, as explained further below.

Most preferably, the detection point is the point at which particles or microfluidic droplets comprising particles are detected for controlling the opening and closing of the oligonucleotide valves as described above, and the detection means is the same.

In a preferred embodiment, the co-localizing channel has a reduced height and/or width or a reduced diameter at the detection point, such that the space for the particle to move vertically and horizontally within the channel (relative to the flow direction) is reduced.

If the particle(s) is comprised in a microfluidic droplet, height and/or width or diameter is/are reduced such that the movement of the droplet is reduced as described for the particle, preferably such that the microfluidic droplet is deformed. Most preferably, the microfluidic droplet forms a plug at the detection point, i.e. it fills the cross-section of the channel and no more than a thin film of the fluid (the immiscible liquid) surrounds the microfluidic droplet. Preferably, the channel at the detection point has less than 100, 90, 70, 60, 50, 40, 30, 20 or less than 10% of the height and/or width or diameter of the rest of the co-localizing channel. Preferably, the height and/or width or diameter at the detection point is between 20 and 50 µm, preferably between 30 and 40 µm, and/or the height and/or width or diameter of the rest of the co-localizing channel is between 50 and 3000 µm, preferably between 50 and 1000 µm or between 50 and 100 µm. A particularly preferred reduced channel height and/or width or diameter, preferably height, of valve-based chips is approximately 50 µm, since this is advantageous for manufacturing. The reduced height and/or width or diameter has the advantage of reducing the floating of the particle out of the focus of the detection means, e.g. the focal plane and/or the centre of the laser spot, thereby reducing the intensities variations of the signal detected, e.g. the emitted light. Therefore, this embodiment is a particularly preferred one.

Further or alternatively, it is also envisaged that the methods of the first aspect comprise feeding a drug into the microchannel. This provides for co-localizing a particle, preferably a cell, a barcode oligonucleotide or components thereof and a drug in a microfluidic droplet. In one embodiment, the drug is fed into the co-localizing channel via the oligonucleotide inlet or at least one oligonucleotide inlet of the set of oligonucleotide inlets together with the barcode oligonucleotide or components thereof. Alternatively, the drug is fed into the co-localizing channel via one of at least two drug inlets which opens and closes together with the oligonucleotide inlet or set of oligonucleotide inlets and is located adjacent to the oligonucleotide inlet or set of oligonucleotide inlets or within the set of oligonucleotide inlets; or opens when the particle passes the drug inlet and closes once it has passed it. In one embodiment, the steps of the method are repeated as described above for a number of particles of the same particle type and for different drugs (providing for drug screening depending on a cell type, i.e. the barcode oligonucleotide tracks the drug so for each barcode oligonucleotide there is a different drug) or for a number of particles of different particle types and for the same drug (providing for cell screening depending on a particular drug, i.e. the barcode oligonucleotide tracks the cell and not the drug). A drug herein can be any substance that may have an effect on a particle, in particular a cell (but also other particles as described above such as viruses), including small molecules, proteins such as ligands, antibodies or antibody derivatives or mimetics, and interfering RNA. The term "drug" also includes a drug combination of one or more such drugs. In one embodiment, a plurality of particles can be co-localized with a barcode oligonucleotide and a drug in the same microfluidic droplet, wherein particles are constantly fed into the co-localizing channel, wherein different valve-operated oligonucleotide inlet or set of valve-operated oligonucleotide inlets open in a time-dependent manner, and wherein a drug is fed into the co-localizing channel as described above.

The term "small molecules" refers to molecules that have a molecular weight between 50 and about 2,500 Daltons, preferably in the range of 200-800 Daltons. In a preferred embodiment, said small molecule is derived from a library, e.g., a small molecule inhibitor library. Small compound libraries include are plurality of chemical compounds and have been assembled from any of multiple sources, including chemically synthesized molecules and natural products, or have been generated by combinatorial chemistry techniques. They may comprise chemical compounds of a particular structure or compounds of a particular organism such as a plant. Generally, small compounds can be derived or selected from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal cell and tissue extracts can be used. Additionally, test compounds can be synthetically produced using combinatorial chemistry either as individual compounds or as mixtures. A collection of compounds made using combinatorial chemistry is referred to herein as a combinatorial library.

The term "antibody" refers to both monoclonal and polyclonal antibodies, i.e., any immunoglobulin protein or portion thereof which is capable of recognizing an antigen or hapten. Exemplary antibodies are IgA, IgD, IgE, IgG, IgM, IgY or IgW. In a particular embodiment, the antibody is produced by an antibody-producing cell, e.g. a B cell or a hybridoma cell, within the same microfluidic droplet.

The term "antibody derivative" as used herein refers to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specifically target binding) antibody fragments such as Fab, Fab2, scFv, Fv, or parts thereof, or other derivatives or combinations of the immunoglobulins such as nanobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent. More preferably, the derivative is a single chain antibody, most preferably having the structure VL-peptide linker-VH or VH-peptide linker-VL.

The term "antibody mimetic" as used herein refers to organic compounds that, like antibodies, can specifically bind antigens, but that are not structurally related to antibodies. They are usually artificial peptides or proteins with a molar mass of about 3 to 20 kDa. Non-limiting examples of antibody mimetics are affibodies, affilins, affimers, affitins, anticalins, avimers, DARPins, fynomers, Kunitz domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, synthetic heterobivalent or heteromultivalent ligands (Josan et al., Bioconjug Chem. 2011 22(7):1270-1278; Xu et al., PNAS 2012 109 (52) 21295-21300; Shallal et al., Bioconjug Chem. 2014 25(2) 393-405) or synthetic peptide ligands, e.g. from a (random) peptide library. Synthetic peptide ligands have non-naturally occurring amino acid sequences that function to bind a particular target molecule. Peptide ligands within the context of the present invention are generally constrained (that is, having some element of structure as, for example, the presence of amino acids which initiate a β turn or β pleated sheet, or for example, cyclized by the presence of disulfide bonded Cys residues) or unconstrained (linear) amino acid sequences of less than about 50 amino acid residues, and preferably less than about 40 amino acids residues. Of the peptide ligands less than about 40 amino acid residues, preferred are the peptide ligands of between about 10 and about 30 amino acid residues.

The term "interfering RNA" or "silencing RNA as used herein includes single-stranded RNA (e.g., mature miRNA, ssRNAi oligonucleotides etc.), double-stranded RNA (i.e., duplex RNA such as siRNA, Dicer-substrate dsRNA, shRNA, aiRNA, or pre-miRNA), a DNA-RNA hybrid (see, e.g., WO 2004/078941), or a DNA-DNA hybrid (see, e.g., WO 2004/104199) that is capable of reducing or inhibiting the expression of a target gene or sequence (e.g., by mediating the degradation or inhibiting the translation of mRNAs which are complementary to the interfering RNA sequence) when the interfering RNA is in the same cell as the target gene or sequence. Interfering RNA thus refers to the single-stranded RNA that is complementary to a target mRNA sequence or to the double-stranded RNA formed by two complementary strands or by a single, self-complementary strand. Interfering RNA may have substantial or complete identity to the target gene or sequence, or may comprise a region of mismatch (i.e., a mismatch motif). The sequence of the interfering RNA can correspond to the full-length target gene, or a subsequence thereof. Preferably, the interfering RNA molecules are chemically synthesized.

In a further preferred embodiment, the methods of the first aspect further comprise fusing the microfluidic droplet comprising the particle comprising DNA and/or RNA and the barcode oligonucleotide or set of components thereof with a microfluidic droplet comprising one or more of: a ligation mix, a primer extension mix, a reverse transcription mix (RT), a PCR mix, an RT-PCR mix, a transposition mix and/or a lysis buffer.

A ligation mix typically comprises ligase (e.g. T4 DNA Ligase), ligase buffer suitable for the ligase used, preferably in ≥1× concentration such that the target droplet contains a 1× concentration (e.g. T4 DNA Ligase buffer, e.g. 2× concentration in the microfluidic droplet before a droplet fusion), all in water, preferably nuclease-free water. A primer extension mix typically comprises polymerase (e.g. Taq Polymerase), polymerase buffer suitable for the polymerase used, preferably in ≥1× concentration such that the target droplet contains a 1× concentration (e.g. Taq Polymerase buffer, e.g. 2× concentration in the microfluidic droplet before a droplet fusion), dNTPs and optionally $MgCl_2$, all in water, preferably nuclease-free water. An RT mix typically comprises reverse transcriptase (e.g. Superscript III RT), reverse transcriptase buffer suitable for the reverse transcriptase used, preferably in ≥1× concentration such that the target droplet contains a 1× concentration (e.g. Superscript 1st strand buffer, e.g. 2× concentration in the microfluidic droplet before a droplet fusion), dNTPs, and optionally RNase inhibitor, all in water, preferably nuclease-free and/or RNase-free water. A PCR mix typically comprises polymerase (e.g. Taq Polymerase), polymerase buffer suitable for the polymerase used, preferably in ≥1× concentration such that the target droplet contains a 1× concentration (e.g. Taq Polymerase buffer, e.g. 2× concentration in the microfluidic droplet before a droplet fusion), dNTPs and optionally $MgCl_2$, all in water, preferably nuclease-free water. An RT-PCR mix typically comprises reverse transcriptase (e.g. Qiagen Sensiscript or Omniscript Reverse Transcriptase), polymerase (e.g. Qiagen HotStar Taq DNA Polymerase), RT-PCT buffer suitable for both enzymes used, preferably in ≥1× concentration such that the target droplet contains a 1× concentration (e.g. Qiagen OneStep RT-PCR Buffer, e.g. 2× concentration in the microfluidic droplet before a droplet fusion), dNTPs, and optionally RNase inhibitor, all in water, preferably nuclease-free and/or RNase-free water. A transposition mix typically comprises transposase (e.g. Tn5 transposase), transposase buffer suitable for the transposase used, preferably in ≥1× concentration such that the target droplet contains a 1× concentration (e.g. Tn5 transposase buffer, e.g. 2× concentration in the microfluidic droplet before a droplet fusion), all in water, preferably nuclease-free water. A lysis buffer comprises substances that lyse the cell but do not destabilize the droplet, preferably a stabilized droplet, for example hydrocarbon detergents such as Tween, SDS, Triton, NP-40 for droplets that are stabilized using (fluoro)surfactants.

In another embodiment, the method of the first aspect further comprises:

sending the microfluidic droplet comprising the particle and the known barcode oligonucleotide or components thereof into a collection channel forming a junction with a waste channel downstream of the co-localizing channel, using a channel selection means, sending at least a portion of the following microfluidic droplets comprising the known barcode oligonucleotide or components thereof into the waste channel using the channel selection means, wherein the channel selection means selects the collection channel before a further microfluidic droplet comprising (i) a particle comprising DNA and/or RNA and (ii) not the same known barcode oligonucleotide arrives at the junction of the collection and waste channel, and wherein the valves of the collection and waste channel are operatively linked to the valves of the oligonucleotide inlets such that microfluidic droplets comprising more than one barcode oligonucleotide or components for more than one barcode oligonucleotide are sent to the waste channel.

In an alternative embodiment, the method of the first aspect further comprises closing the preferably valve-operated inlet that feeds the particles into the microfluidic channel for a time to avoid particles passing the series of oligonucleotide inlets at the time when one of the oligonucleotide inlets closes and another opens, to avoid co-localizing a particle with oligonucleotides from more than one oligonucleotide inlet or more than one set of oligonucleotide inlets, i.e. oligonucleotides that are or allow for forming more than one barcode oligonucleotide. This avoids the generation of microfluidic droplets comprising a particle and more than one barcode oligonucleotide or components for more than one barcode oligonucleotide, and can be achieved by operatively linking the valve-operated inlet that feeds the particles into the microfluidic channel with the series of valve-operated oligonucleotide inlets. While this alternative embodiment is possible, it is less preferable, because if the particles are cells, it may lead to cell clumps and an inhomogeneous cell distribution in the channel.

In the embodiment in which potentially a plurality of particles is co-localized with a barcode oligonucleotide and a drug in the same microfluidic droplet, it is particularly preferred that the method further comprises:

sending the microfluidic droplet comprising the particle(s) and the known barcode oligonucleotide or components thereof into a collection channel forming a junction with a waste channel downstream of the co-localizing channel, using a channel selection means, sending at least a portion of the following microfluidic droplets comprising the known barcode oligonucleotide or components thereof into the waste channel using the channel selection means, wherein the channel selection means selects the collection channel before a further microfluidic droplet comprising (i)

one or more particles and (ii) not the same known barcode oligonucleotide arrives at the junction of the collection and waste channel, and wherein the valves of the collection and waste channel are operatively linked to the valves of the oligonucleotide inlets such that microfluidic droplets comprising more than one barcode oligonucleotide or components for more than one barcode oligonucleotide are sent to the waste channel.

In the embodiment in which potentially a plurality of particles is co-localized with a barcode oligonucleotide and a drug in the same microfluidic droplet, it is alternatively also possible but less preferred that the method further comprises closing the preferably valve-operated inlet that feeds the particles into the microfluidic channel for a time to avoid particles passing the series of oligonucleotide inlets at the time when one of the oligonucleotide inlets closes and another opens, to avoid co-localizing one or more particles to be enclosed in one microfluidic droplet with oligonucleotides from more than one oligonucleotide inlet or more than one set of oligonucleotide inlets, i.e. oligonucleotides that are or allow for forming more than one barcode oligonucleotide. This avoids the generation of microfluidic droplets comprising one or more particles and more than one barcode oligonucleotide or components for more than one barcode oligonucleotide, and can be achieved by operatively linking the valve-operated inlet that feeds the particles into the microfluidic channel with the series of valve-operated oligonucleotide inlets.

The term "sending the microfluidic droplet" refers to selecting a channel with the channel selection means such that the flow/fluid of the co-localizing channel and/or a microfluidic droplet is directed to the respective channel.

The term "channel selection means" refers to any sorting force or manipulation means, which can be based on dielectrophoresis (X. Hu et al., Marker-specific sorting of rare cells using dielectrophoresis. Proc Natl Acad Sci USA 102, 15757 (Nov. 1, 2005), valves (A. Y. Fu, C. Spence, A. Scherer, F. H. Arnold, S. R. Quake, A microfabricated fluorescence-activated cell sorter. Nat Biotechnol 17, 1109 (November 1999)), optics (Z. C. Landry, S. J. Giovanonni, S. R. Quake, P. C. Blainey, Optofluidic cell selection from complex microbial communities for single-genome analysis. Methods in enzymology 531, 61 (2013)), acoustics (L. Schmid, D. A. Weitz, T. Franke, Sorting drops and cells with acoustics: acoustic microfluidic fluorescence-activated cell sorter. Lab on a Chip 14, 3710 (Oct. 7, 2014)) or stream deflection, preferably electric stream deflection (P. S. Dittrich, P. Schwille, An integrated microfluidic system for reaction, high-sensitivity detection, Anal Chem.; 75(21): 5767-74. (2003)). Accordingly, the sorting force or manipulation means may be a DEP sorting force or manipulation means, an acoustophoresis sorting force or manipulation means, a microvalve-based sorting force or manipulation means, a piezoelectric sorting force or manipulation means, or a dynamic stream deflection sorting force or manipulation means. Preferred is a microvalve-based sorting force or manipulation means.

The phrase "at least a portion" means at least those droplets that contain more than one different barcode oligonucleotide or components for more than one barcode oligonucleotide, wherein there is more than a trace of the more or one different barcode oligonucleotide or the components for more than one barcode oligonucleotide. "More than a trace" means more than 5, more than 3, more than 2, more than 1, more than 0.5, more than 0.3, more than 0.2 or more than 0.1% of the total mass or amount of molecules of barcode oligonucleotides or of components for barcode oligonucletides. This is for the situation in which an oligonucletide inlet opens before all barcode oligonucleotides or components thereof fed from upstream and previously open (now closing) oligonucletide inlets pass the just opened oligonucletide inlet. Usually unsupposedly (e.g. because the particles are not spaced out to an appropriate distance), but not necessarily so (see the method of the fourth aspect) one or more other further particles could be passing the series of oligonucleotides inlets at this time. In such a situation, barcode oligonucleotides or components thereof which are not meant to be co-localized are co-localized, and possibly also co-localized with such a further particle. These will be flushed into the waste channel by operatively linking the channel selection means with the valve-operated oligonucleotide inlets.

The term "operatively linked" means that the channel selection means is coordinated with the valves of the valve-operated oligonucleotide inlets, such that droplets containing two different barcode oligonucleotides or components for more than one barcode oligonucleotide are directed into the waste channel. The coordination may be by time, e.g. the channel selection means selects the waste channel for a certain time whenever switching the valve configuration from adding one oligonucleotide (or a given set of components) to another one. After said certain time all droplets are collected before the cycle starts again when switching to yet another oligonucleotide (or another set of components). The "certain time" depends on the flow speed in the channel and the distance from the oligonucleotide inlets to the channel selection means. In a typical setup, it is about 0.1 to 5 seconds, about 0.1 to 3 seconds or preferably about 0.1 to 1 seconds, for example about 0.5 seconds. With regard to the further valve-operated inlet (particle inlet) upstream of the series of valve-operated inlets (oligonucleotide inlets) it means the opening and closing of the particle inlet is coordinated with the oligonucleotide inlets such that particles are not co-localized in a droplet with two different barcode oligonucleotides or components for more than one barcode oligonucleotide. The coordination may be by time, which depends on the flow speed in the channel and the distance from the oligonucleotide inlets to the channel selection means. In a typical setup, it is about 0.1 to 15 seconds, about 0.5 to 10 seconds or preferably about 1 to 5 seconds, for example about 3 seconds.

The phrase "comprising more than one barcode oligonucleotide or components for more than one barcode oligonucleotide" refers to comprising more than one barcode oligonucleotide or components for more than one barcode oligonucleotide of one identity or sequence (not molecules), i.e. to having two or more barcode oligonucleotide or components with different sequences, in particular in the variable regions.

In a particular embodiment thereof, the channel selection means selects the collection channel before a further microfluidic droplet comprising a particle and a known marker oligonucleotide or components thereof arrives at the junction of the collection and waste channel. Alternatively or additionally, the channel selection means selects the collection channel after all microfluidic droplets comprising (preferably traces, as defined above, of) more than one barcode oligonucleotide or components for more than one barcode oligonucleotide have been sent to the waste channel.

Preferably, this embodiment comprises
sending the microfluidic droplet comprising the particle and the known barcode oligonucleotide or components thereof into a valve-operated collection channel forming a junction with a valve-operated waste channel downstream of the co-localizing channel, sending at least a portion of the following microfluidic droplets comprising the known barcode oligonucleotide or components thereof into a valve-operated waste channel by closing the valve of the collection channel and opening the closed valve of the waste channel, wherein the valves of the collection and waste channel are operatively linked to the valves of the oligonucleotide inlets such that microfluidic droplets comprising more than one barcode oligonucleotide or components for more than one barcode oligonucleotide are sent to the waste channel.

In a particular embodiment thereof, the valve of the collection channel opens and the valve of the waste channel closes before a further microfluidic droplet comprising a particle and a known barcode oligonucleotide or components thereof arrive(s) at the junction of the collection and waste channel. Alternatively or additionally, the valve of the collection channel opens and the valve of the waste channel closes after all microfluidic droplets comprising more than one barcode oligonucleotide or components for more than one barcode oligonucleotide have been sent to the waste channel.

In a preferred embodiment, the method of the first aspect further comprises after the ligation step, in case the DNA and/or RNA comprised by the particle is not accessible by the barcode oligonucleotide, disrupting the particle such that the DNA and/or RNA is accessible by the barcode nucleotide. For example if the particle is a cell, the cell is lysed, e.g. with a short laser pulse which does not inactivate enzymes, with ultrasound or by fusing the droplet with a microfluidic droplet comprising a lysis buffer.

In another preferred embodiment of the methods of the first aspect, the known barcode oligonucleotide is generated in the microfluidics system. Preferably, generating the known barcode oligonucleotide comprises:

(a) feeding a first oligonucleotide into an oligonucleotide channel terminating at a oligonucleotide inlet of a set of the at least two sets of oligonucleotide inlets, wherein the first oligonucleotide comprises an optional priming region (or alternatively inverted repeats of transposable elements), a variable region and a single-stranded annealing region, (b) optionally feeding one or more sequential internal oligonucleotides into a further oligonucleotide channel each, each oligonucleotide channel terminating at a further oligonucleotide inlet of the set of (a), wherein each sequential internal oligonucleo tide comprises a variable region between two single-stranded annealing regions, (c) feeding a terminal oligonucleotide into a further oligonucleotide channel terminating at a further oligonucleotide inlet of the set of (a), wherein the terminal oligonucleotide comprises a single-stranded annealing region, a variable region and optionally a priming region (or alternatively inverted repeats of transposable elements), wherein the single-stranded annealing regions are overlapping complementary sequences enabling the annealing of the first oligonucleotide, the optional one or more sequential internal oligonucleotides, and the terminal oligonucleotide in this order into a single linear oligonucleotide, (d) annealing the first oligonucleotide, the optional one or more sequential internal oligonucleotides, and the terminal oligonucleotide together in this order into a single linear and at least partially double-stranded oligonucleotide via the overlapping annealing regions downstream of the oligonucleotide inlets, (e) optionally, if the single linear oligonucleotide is partially double-stranded, extending double-stranded portions of the partially double-stranded oligonucleotide and/or filling gaps in the partially double-stranded oligonucleotide enzymatically, and (f) ligating the annealed first oligonucleotide, the optional one or more sequential internal oligonucleotides, and the terminal oligonucleotide, or, if the first oligonucleotide is annealed directly to the terminal nucleotide, extending double-stranded portions of the resulting partially double-stranded oligonucleotide.

It is also envisaged that, alternatively, generating the known barcode oligonucleotide comprises:

(a) feeding a first oligonucleotide into an oligonucleotide combination channel terminating at one of the at least two valve-operated oligonucleotide inlets, wherein the first oligonucleotide comprises an optional priming region (or alternatively inverted repeats of transposable elements), a variable region and a single-stranded annealing region, (b) optionally feeding one or more sequential internal oligonucleotides into the oligonucleotide combination channel, wherein each sequential internal oligonucleotide comprises a variable region between two single-stranded annealing regions, (c) feeding a terminal oligonucleotide into the oligonucleotide combination channel, wherein the terminal oligonucleotide comprises a single-stranded annealing region, a variable region and optionally a priming region (or alternatively inverted repeats of transposable elements), wherein the single-stranded annealing regions are overlapping complementary sequences enabling the linking of the first oligonucleotide, the optional one or more sequential internal oligonucleotides, and the terminal oligonucleotide in this order into a single linear oligonucleotide, and (d) annealing the first oligonucleotide, the optional one or more sequential internal oligonucleotides, and the terminal oligonucleotide together in this order into a single linear and at least partially double-stranded oligonucleotide via the overlapping annealing regions downstream of the oligonucleotide inlets, and (e) optionally, if the single linear oligonucleotide is partially double-stranded, extending double-stranded portions of the partially double-stranded oligonucleotide and/or filling gaps in the partially double-stranded oligonucleotide enzymatically, and (f) ligating the annealed first oligonucleotide, the optional one or more sequential internal oligonucleotides, and the terminal oligonucleotide, or, if the first oligonucleotide is annealed directly to the terminal nucleotide, extending double-stranded portions of the resulting partially double-stranded oligonucleotide.

For this approach, it is preferred that the feeding in steps (a) to (c) is via sets of valve-operated inlets as described above (each set comprising a oligonucleotide of (a), (b), and (c)), and that they are controlled and coordinated as the sets of oligonucleotide inlets described above. In addition, these sets of valve-operated inlets are coordinated with the valve-operated oligonucleotide the oligonucleotide combination channel terminates at, such that when said valve-operated oligonucleotide inlet opens, one set of barcode oligonucleotides or a barcode oligonuceotide assembled in the combination channel is fed into the co-localizing channel. It is preferred that while (and only when) said valve-operated oligonucleotide inlet is closed, a waste valve is open through which the contents of the combination channel are flushed.

Preferably, in both approaches:

in (a) the first oligonucleotide is chosen from one of at least 2, 4, 8, or even at least 16, 32, or 64 first oligonucleotides having the same priming region (or alternatively inverted repeats of transposable elements), different variable regions and the same annealing region, in (b) the one or more sequential internal oligonucleotide are each chosen from at least 2, 4, 8, or even at least 16, 32, or 64 internal oligonucleotides having different variable regions and the same annealing regions, wherein the annealing regions differ between sequential internal oligonucleotides, and in (c) the terminal oligonucleotide is chosen on one of at least 2, 4, 8, or even at least 16, 32, 64 or 96 terminal oligonucleotides having the same annealing region, different variable regions and the same optional priming region (or alternatively inverted repeats of transposable elements).

The length of the variable regions, the annealing regions and/or of the priming regions (or alternatively inverted repeats of transposable elements) is preferably 1 to 50 nucleotides, more preferably 1 to 20 nucleotides and most preferably 2 to 10 nucleotides. Generally, the choice of the oligonucleotides chosen in (a), (b) and (c) can be pre-determined or random, and the choice, in particular the random choice, is recorded. This choice, preferably the random choice, always leads to a new combination of the oligonucleotides chosen in (a), (b) and (c).

The term "first oligonucleotide" refers to an oligonucleotide which comprises an optional priming region (or alternatively inverted repeats of transposable elements), a variable region and an annealing region in this order. The priming region is double- or single-stranded, preferably single-stranded, the variable region is preferably double-stranded and the annealing region is single-stranded. The priming region has (i) a 5' poly-T sequence (of the sense or antisense strand with respect to the double-stranded variable region) for annealing to poly-adenylated mRNA, provided the particle comprises mRNA and the mRNA or the transcriptome is to be barcoded (unless the terminal oligonucleotide comprises a 3' poly-G sequence as described below for analyzing mRNA, in this case the first oligonucleotide lacks a priming region), or (ii) a sequence that is complementary to a sequence of the DNA or RNA the particle comprises. The priming region is identical for all first oligonucleotides. Instead of a priming region, the first oligonucleotide can comprise inverted repeats of transposable elements (e.g., for a transposition reaction). The variable region is unique for each first oligonucleotide. The annealing region is identical for all first oligonucleotides and it is complementary to the annealing region of an internal oligonucleotide, if present, or to the annealing region of the terminal oligonucleotide, if there are no internal oligonucleotides.

The term "internal oligonucleotide" refers to an oligonucleotide which comprises a variable region between two annealing regions. There may be one or more internal oligonucleotides and if there is more than one, the internal oligonucleotides have annealing regions which enable the sequential linking of all internal oligonucleotides. The first internal oligonucleotide has a preferably single-stranded first annealing region, which is identical for all first internal oligonucleotides and is complementary to the annealing region of the first oligonucleotide, a preferably double-stranded variable region, which is unique for each first internal oligonucleotide, and a preferably single-stranded second annealing region, which is identical for all first internal oligonucleotides and is complementary to the first annealing region of either a further internal nucleotide or, if there is none, to the annealing region of the terminal oligonucleotide. The last internal oligonucleotide, if there are at least two internal oligonucleotides, has a preferably single-stranded first annealing region, which is identical for all last internal oligonucleotides and is complementary to the second annealing region of the first internal oligonucleotide or of a possible further internal oligonucleotide, a preferably double-stranded variable region, which is unique for each last internal oligonucleotide, and a preferably single-stranded second annealing region, which is identical for all first internal oligonucleotides and is complementary to the first annealing region of the terminal oligonucleotide. Further internal oligonucleotides have two preferably single-stranded annealing regions and, between them, one preferably double-stranded variable region, wherein the first annealing region is the same for each further internal oligonucleotide, the second annealing region is the same for each further internal oligonucleotide, and the variable region is unique for each further internal oligonucleotide. The annealing regions are each complementary to one annealing region of one other internal oligonucleotide, such that all internal oligonucleotide can be annealed in only one way to a chain of internal nucleotides with two single-stranded annealing regions, one of which is complementary to the annealing region of the first oligonucleotide, and the other one is complementary to the annealing region of the terminal oligonucleotide.

The term "terminal oligonucleotide" refers to an oligonucleotide which comprises an annealing region, a variable region and an optional priming region (or alternatively inverted repeats of transposable elements) in this order. The optional priming region is preferably single-stranded, the variable region is double- or single-stranded, preferably double-stranded and the annealing region is single-stranded. The annealing region is identical for all terminal oligonucleotides and it is complementary to the annealing region of an internal oligonucleotide, if present, or to the annealing region of the first oligonucleotide, if there are no internal oligonucleotides. The variable region is unique for each terminal oligonucleotide. The optional priming region has (i) a 3' poly-G sequence (of the sense or antisense strand with respect to the double-stranded variable region) for annealing to a cDNA which is synthesized from poly-adenylated mRNA using a poly-T primer and which is modified by terminal transferase activity by having deoxycytidines added to the 3' end of the cDNA (SMART mRNA transcription), provided the particle comprises mRNA and the mRNA or the transcriptome is to be analyzed, or (ii) a sequence that is complementary to a sequence of the DNA or RNA the particle comprises. The priming region is identical for all terminal oligonucleotides. The terminal oligonucleotide comprises a priming region if the barcode oligonucleotide is to be suitable for generating an amplificate from the DNA or RNA comprised by the particle. In this case, also the priming region of the first oligonucleotide has a sequence that is complementary to a sequence of the DNA or RNA the particle comprises. Each of the two priming regions is then on a different strand of the barcode oligonucleotide and, together, the priming regions form a primer pair for generating an amplificate from the DNA or RNA comprised by the particle. Instead of a priming region, the terminal oligonucleotide can comprise inverted repeats of transposable elements (e.g., for a transposition reaction).

Generally, a barcode oligonucleotide comprises either one priming region (in the first or terminal oligonucleotide, e.g. for a reverse transcription), two priming regions (one in the first and in the terminal oligonucleotide, e.g. for a PCR), or two transposable elements (one in the first and in the terminal oligonucleotide, e.g. for a transposition reaction). Inverted repeats of transposable elements preferably are 3' and 5' end sequences at the ends of the barcode oligonucleotide. An example are the 19 bp Tn5 end sequences for Tn5 transposition (see Goryshin and Reznikoff, J Biol Chem. 1998 Mar. 27; 273(13):7367-74).

In a preferred embodiment, first oligonucleotide, one of the internal oligonucleotides or the terminal oligonucleotide comprises a unique molecular identifier (UMI). A "UMI" is an oligonucleotide sequence which is unique (or random with a length that makes uniqueness likely) for each terminal oligonucleotide molecule. This can improve reliability of amplification and reduce amplification noise (see, e.g. S. Islam et al., Quantitative single-cell RNA-seq with unique molecular identifiers. *Nature methods* 11, 163, February 2014).

The phrase "overlapping sequences enabling the linking" refers to single-stranded annealing regions as defined above, which are each complementary to only one other annealing region. This way, the oligonucleotides can only be linked to a single linear oligonucleotide and not to several different linear oligonucleotides.

The term "single linear oligonucleotide" refers to an at least partly double-stranded oligonucleotide. Partly double-stranded means that at least the priming region(s) is/are single-stranded. However, other parts may also be single-stranded, i.e. there may be single-stranded gaps within the double-stranded part.

The term "enzymatically" refers to the use of an enzyme to extend double-stranded portions of the partially double-stranded oligonucleotide and/or to fill gaps in the partially double-stranded oligonucleotide. Double-stranded portions are extended and gaps are filled preferably with a DNA polymerase that has no strand displacement activity, such as Taq polymerase.

In a second aspect, the invention relates to a method for barcoding the transcriptome of a cell, for barcoding a DNA amplificate from a cell or for barcoding the genome of a cell, comprising the steps of
(i) co-localizing a cell with a known barcode oligonucleotide in a microfluidic droplet using the method of the first aspect,
(ii) lysing the cell in the microfluidic droplet, and
(iii) annealing the barcode oligonucleotide to RNA or DNA of the lysed cell in the microfluidic droplet,
(iv) carrying out a reverse transcription (RT), RT-PCR, PCR, or a transposition reactionusing the annealed barcode oligonucleotide as primer(s) or transposable elements, respectively, in the microfluidic droplet or in an aqueous phase in which the microfluidic droplet is disrupted, thereby generating a barcoded transcriptome, DNA amplificate or genome,
wherein an RT mix, an RT-PCR mix, a PCR mix, or a transposition mix, respectively, is comprised in the co-localizing channel in step (i), is comprised in a microfluidic droplet fused to the microfluidic droplet of step (i), (ii) or (iii) or is comprised in an aqueous phase in which the microfluidic droplet is disrupted.

Therein, the barcode preferably comprises at least one priming region or alternatively transposable elements.

In a preferred embodiment, the method is for barcoding the transcriptome of a single cell or for barcoding a DNA amplificate from a single cell or for barcoding the genome of a single cell, wherein in step (i) a single cell is co-localized with a known barcode oligonucleotide in a microfluidic droplet.

In another preferred embodiment, the method of the second aspect further comprises the steps of:
(v) inactivating any enzymes of the microfluidic droplet comprising the barcode oligonucleotide and disrupting the microfluidic droplet in any order, and
(vi) analyzing the barcoded transcriptome or barcoded DNA amplificate or barcoded genome.

Preferably, the microfluidic droplet is pooled with one or more further microfluidic droplets after step (iii) or (iv) (preferably after step (iii)), or the contents of the microfluidic droplet are pooled with the contents of one or more further microfluidic droplets between step (iii), (iv) or and (v) (preferably after step (iv) or (v)), wherein the one or more further microfluidic droplets are generated with the same method carried out with a different barcode oligonucleotide each, and wherein the transcriptomes or DNA amplificates or genomes of all microfluidicdroplets is/are analyzed in parallel.

The term "transcriptome", as referred to herein, means the collection of all mRNA molecules of a cell. The term "barcoded transciptome" refers to the cDNA generated from a transcriptome with a barcode oligonucleotide e.g. having one priming region with a 5' poly-T sequence as described above as a reverse transcription primer.

Thus, "barcoding a transcriptome" means generating cDNA from a transcriptome with a barcode oligonucleotide having one priming region with a 5' poly-T sequence as described above as a reverse transcription primer. Alternatively, "barcoding a transcriptome" can also mean generating a cDNA from a transcriptome with a barcode oligonucleotide having one priming region with a 3' poly-G sequence which is processed by a template switching reverse transcriptase with terminal transferase activity (e.g. Clontech SMART system). Such a SMART mRNA transcription begins with the generation of a double-stranded cDNA template. As a first step, nanogram quantities of total RNA and a modified oligo(dT) primer (the cDNA Synthesis Primer II A) are used to initiate first-strand cDNA synthesis. When the reverse transcriptase (RT) reaches the 5' end of the mRNA, the enzyme's terminal transferase activity adds a few additional nucleotides, primarily deoxycytidine, to the 3' end of the cDNA. The SMART T7 Oligonucleotide, which has an oligo(G) sequence at its 3' end, base-pairs with the deoxycytidine stretch, creating an extended template. RT then switches templates and continues replicating to the end of the oligonucleotide. The resulting full-length, single-stranded (ss) cDNA contains sequences that are complementary to the SMART T7 Oligonucleotide. The SMART T7 anchor sequence is then used for primer extension to generate double-stranded cDNA.

"Barcoding a DNA amplificate" means generating a DNA amplificate with a barcode oligonucleotide having two priming regions as described above as a primer pair (each strand of the barcode oligonucleotide is a primer). "Barcoding a genome" refers to introducing barcodes using barcoded oligonucleptides during an in vitro transposition step as referred to herein (e.g. Illumina Nextera technology)

In step (v), enzymes are inactivated to prevent enzyme activity, such as polymerase or reverse transcriptase activity, using components (primers, DNA, or RNA) of the microfluidic droplet with primers, DNA, or RNA which was/were not comprised in the same microfluidic droplet (e.g. which was comprised in a different microfluidic droplet if droplets are pooled). Enzymes can be inactivated, for example, by changing the temperature (e.g. heat inactivation), the pH, the buffer composition or by adding enzyme-specific inhibitors to achieve conditions under which the enzyme does not function. Accordingly, inactivation can occur before droplet disruption (e.g. heat inactivation) or after droplet disruption (e.g. disrupting the droplet in an aqueous phase with an inactivating pH, buffer or with enzyme inhibitors). The droplets are disrupted, i.e. the barcoded transcriptome or barcoded DNA amplificate or barcoded genome is released into an aqueous phase, preferably by the addition of a destabilizing agent, for example the emulsion destabilizer A104 (RainDance Technologies, as described in Clausell-Tormos et al., Droplet-based microfluidic platforms for the encapsulation and screening of mammalian cells and multicellular organisms, Chem Biol, vol 15, pg 427, 2008).

"Analyzing the transcriptome or DNA amplificate or genome" preferably comprises sequencing. "Analyzing in parallel" refers to analyzing the pooled barcoded transcriptomes or pooled barcoded DNA amplificates or barcoded genomes together, preferably by next-generation sequencing. This allows performing only one analysis step, such as one sequencing reaction, for all cells to be analysed, instead of a separate analysis for each cell to be analysed.

Preferably, in the method of the second aspect, step (iv) is carried out in the microfluidic droplet and/or (preferably and) an RT mix, an RT-PCR mix, a PCR mix, or a transposition mix, respectively, is comprised in a microfluidic droplet fused to the microfluidic droplet after step (i).

Thus, in a preferred embodiment, the method of the second aspect comprising the steps of
(i) co-localizing a cell with a known barcode oligonucleotide in a microfluidic droplet using the method of the first aspect,
(ii) lysing the cell in the microfluidic droplet,
(iii) annealing the barcode oligonucleotide to RNA or DNA of the lysed cell in the microfluidic droplet,
(iv) carrying out a reverse transcription (RT), RT-PCR, PCR or transposition reaction using the annealed barcode oligonucleotide as primer(s) or transposable elements, respectively, in the microfluidic droplet, thereby generating a barcoded transcriptome or DNA amplificate, wherein an RT mix, an RT-PCR mix, a PCR mix, or a transposition mix, respectively, is comprised in a microfluidic droplet fused to the microfluidic droplet of step (i), (ii) or (iii).

All other terms are to be understood as described for the method of the first aspect.

The method of the second aspect can also be described as a method for co-localizing a cell comprising DNA and/or RNA with a known barcode oligonucleotide or set of components thereof in a microfluidic droplet in a microfluidics system comprising the steps defined for the method of the first aspect and, in addition, the steps of the method of the second aspect (obviously without step (i) and wherein the microfluidic droplet is the droplet resulting from the steps of the method of the first aspect).

In a third aspect, the present invention relates to a method for correlating the phenotype of a single cell with its transcriptome, with a DNA amplificate derived from the cell or with its genome, comprising barcoding the transcriptome of a single cell, barcoding a DNA amplificate from a single cell or barcoding the genome of a single cell using the method of the third aspect, wherein the cell is phenotyped in step (i), and wherein the sequence of the barcode in the barcoded transcriptome, amplificate or genome indicates the phenotype of the cell from which the transcriptome, DNA amplificate or genome is derived.

All terms are to be understood as described for the methods of the first and second aspect.

The method of the third aspect can also be described as a method for co-localizing a cell comprising DNA and/or RNA with a known barcode oligonucleotide or set of components thereof in a microfluidic droplet in a microfluidics system comprising the steps defined for the method of the first aspect and, in addition, the steps of the method of the second aspect (obviously without step (i) and wherein the microfluidic droplet is the droplet resulting from the steps of the method of the first aspect), wherein the cell is phenotyped at the detection point, and wherein the sequence of the variable regions of the barcode oligonucleotide in the transcriptome, the amplificate or the genome indicates the cell from which the transcriptome or the DNA amplificate is derived.

In a fourth aspect, the present invention relates to a method for determining the effect of a drug on the transcriptome of a cell or on an DNA amplificate from a cell, comprising barcoding a transcriptome of a cell or a DNA amplificate from a cell using the method of the second aspect including steps (v) and (vi), wherein the DNA amplificate is generated from mRNA by RT-PCR, wherein a known drug is fed into the microchannel in step (i) of the second aspect, and wherein the sequence of the barcode in the barcoded transcriptome or the barcoded DNA amplificate indicates the drug to which the cell was exposed or the cell which was exposed to the drug.

Therein, the known drug is co-localized with the known barcode oligonucleotide and the cell.

It is envisaged that in the method of the fourth aspect, the cell can be phenotyped to correlate the phenotype of the cell before or after the drug takes effect with the transcriptome or a DNA amplificate derived from the cell as described in the method of the third aspect and, thereby, to analyze the drug effect specific to the cell phenotype. In this embodiment, the effect on the transcriptome on the cell or amplificate from the cell is determined for a single cell. "Before the drug takes effect" relates to a phenotyping at the detection point as described above for the method of the third aspect. "After the drug takes effect" refers to a phenotyping after an incubation time (e.g. up to 1 to 6, 12, 14, 48 or even 72 hours). This can be done outside of the microfluidic device, after which the droplets are inserted into a microfluidic device comprising a suitable detection means and possible sorting the droplets for a particular cell phenotype. For example, one could incubate with chemotherapeutic drugs (barcoded by oligonucleotides), specifically sort the resistant cells (a resistant phenotype could be coupled to a fluorescence signal of the droplets) and analyze their transcriptome.

Generally, however, the method of the fourth aspect can determine the effect on the transcriptome of or in the amplificate from a single cell or a plurality of cells. If a plurality of cells is examined, cells are fed into the co-localizing channel at a higher density such that several cells can be co-localized with the known barcode oligonucleotide and the drug in the same or in several microfluidic droplet(s) (including single-cell droplets). In this embodiment, the valves of the valve-operated oligonucleotide inlets open and close independent on whether a cell is passing or has passed the series of oligonucleotide inlets. Instead, they open and close in a time-dependent manner. For this embodiment, it is particularly preferred that the method further comprises:

sending the microfluidic droplet comprising the cell(s), the known barcode oligonucleotide or components thereof and the drug into a collection channel forming a junction with a waste channel downstream of the co-localizing channel, using a channel selection means, sending at least a portion of the following microfluidic droplets comprising the known barcode oligonucleotide or components thereof and the drug into the waste channel using the channel selection means, wherein the channel selection means selects the collection channel before a further microfluidic droplet comprising (i) one or more cells and (ii) not the same known barcode oligonucleotide and/or not the same drug arrives at the junction of the collection and waste channel, and wherein the valves of the collection and waste channel are operatively linked to the valves of the oligonucleotide inlets such that microfluidic droplets comprising more than one barcode oligonucleotide or components for more than one barcode oligonucleotide or more than one drug are sent to the waste channel.

The phrase "at least a portion" means at least those droplets that contain more than one different barcode oligonucleotide or components for more than one barcode oligonucleotide, or more than one drug, wherein there is more than a trace of the more or one different barcode oligonucleotide or the components for more than one barcode oligonucleotide, or more than one drug. "More than a trace" means more than 5, more than 3, more than 2, more than 1, more than 0.5, more than 0.3, more than 0.2 or more than 0.1% of the total mass or amount of molecules of barcode oligonucleotides or of components for barcode oligonucleotides, or of drugs. This is for the situation in which an oligonucletide or drug inlet opens before all barcode oligonucleotides or components thereof or drugs fed from upstream and previously open (now closing) inlets pass the just opened inlet or the droplet maker.

The term "operatively linked" means that the channel selection means is coordinated with the valves of the valve-operated oligonucleotide and/or drug inlets, such that droplets containing two different barcode oligonucleotides or components for more than one barcode oligonucleotide or two drugs are directed into the waste channel. Similarly, all embodiments described above with respect to the control of the oligonucleotide inlets and/or the channel selection means are included here with a corresponding control and/or selection of the drug inlets (i.e. having "or drug inlet" and "or drug" as an alternative to the barcode oligonucleotide inlets and barcode oligonucleotides).

Otherwise, all terms are to be understood as described for the methods of the first and second aspect.

The method of the fourth aspect can also be described as a method for co-localizing a cell comprising DNA and/or RNA with a known barcode oligonucleotide or set of components thereof in a microfluidic droplet in a microfluidics system comprising the steps defined for the method of the first aspect and, in addition, the steps of the method of the second aspect including steps (v) and (vi) (obviously without step (i) and wherein the microfluidic droplet is the droplet resulting from the steps of the method of the first aspect), wherein the DNA amplificate is generated from mRNA by RT-PCR, wherein a known drug is fed into the microchannel and co-localized with the cell and the barcode oligonucleotide or components thereof, and wherein the sequence of the variable regions of the barcode oligonucleotide in the transcriptome or the amplificate indicates the drug to which the cell was exposed.

In a fifth aspect, the invention relates to a microfluidic device, comprising a microfluidic channel comprising a series of at least two valve-operated aqueous fluid inlets or sets of valve-operated aqueous fluid inlets for feeding an aqueous fluid into the microfluidic channel, an immiscible fluid inlet downstream of the series of at least two aqueous fluid inlets or sets of aqueous fluid inlets for feeding an immiscible fluid into the microfluidic channel to generate microfluidic droplets, (i) a collection channel and a waste channel forming a junction downstream of the microfluidic channel, and a channel selection means, or (ii) a further valve-operated aqueous fluid inlet upstream of the series of at least two valve-operated aqueous fluid inlets or sets of valve-operated aqueous fluid inlets, wherein only one of the at least two valve-operated aqueous fluid inlets or sets of valve-operated aqueous fluid inlets is open at any one time, characterized in that (i) the channel selection means is operatively linked to the valves of the aqueous fluid inlets such that microfluidic droplets comprising what is fed into the microfluidic channel by more than one of the at least two aqueous fluid inlets or sets of aqueous fluid inlets are sent either to the waste or the collection channel, preferably to waste channel; or (ii) the further valve-operated aqueous fluid inlet is operatively linked to the valves of the aqueous fluid inlets of the series of at least two valve-operated aqueous fluid inlets or sets of valve-operated aqueous fluid inlets such that the further valve-operated aqueous fluid inlet closes to avoid that microfluidic droplets comprising what is fed into the microfluidic channel by more than one of the at least two aqueous fluid inlets or sets of aqueous fluid inlets also comprise what is fed into the microfluidic channel by the further valve-operated aqueous fluid inlet, and then opens.

In a preferred embodiment, the aqueous fluid inlets of said series are oligonucleotide inlets and the further aqueous fluid inlet is a particle inlet as described for the method of the first aspect. All terms are to be understood as described for the methods of the first and second aspect. Also, all embodiments described for the methods of the invention also apply to the device of the invention, in as far as applicable.

Apart from the features described with respect to the above aspects of the invention, the device of the fifth aspect may also comprise one or more integrated electrodes, microvalves, micropumps, droplet generators and/or a laser spectroscopy setup. "Integrated" means embedded between two layers of device material as specified above (e.g. glass or PDMS) or placed on top of the device, preferably a chip.

Generally, electrodes can enable on-chip functionalities such as electrical impedance spectrometry, electrophoresis, amperometric detection, temperature sensing, electrical heating (e.g. to provide a temperature suitable for maintaining cells, such as about 34-40° C., 35-39° C., 36-38° C. or preferably about 37° C.), generating electroosmotic flow and/or high voltage microfluidic experimentation. Exemplary electrodes are field electrodes, detection electrodes, and heating and sensing electrodes. Field electrodes are used to conduct electrical current and generate electrical fields for controlling electroosmotic flows. Detection electrodes are used to measure the local electrical conductivity or impedance of the liquid in a fluidic channel. Detection electrodes can in particular be used for example to count and characterize particles, especially cells, in microfluidic droplets. Heating and sensing electrodes are used as electrical heaters and temperature sensors on a chip to provide a convenient means to heat fluids inside microchannels and measure the temperature. This is particularly useful if the microfluidic droplets contain cells, i.e. if the particles of the aspects of the invention are cells. While heating and sensing electrodes can be used independently from each other, i.e. while the device can comprise heating or sensing electrodes, it is preferred that it comprises both and even more preferred that they are functionally coupled and that the heating electrodes are controlled by a feedback loop according to temperatures measured with the sensing electrodes such that a desired temperature is maintained, in particular a temperature suitable for maintaining cells as described above. Between electrodes and microfluidic channels, insulating layers can be applied.

For the meaning of "microvalve", see above.

The term "micropump", as used herein, refers to a structure that can provide force for displacement of liquids or gases within a microchannel. A wide variety of pumping mechanisms are known in the art. Preferably, the "micropump" is of a positive displacement type wherein the pump generates a positive pressure, above the atmospheric pressure, and the higher pressure is coupled to at least one microfluidic channel. The differential pressure causes movement of the gas or liquid. An "integrated micropump", also known as "integrated pressure source", "on-chip micropump" or "on-chip pressure source", refers to a micropump configuration that is an integral part of the microfluidic device and is preferably irreversibly attached to it. Thus, in the microfluidic device of the invention, micropumps are responsible for generating temporal and volumetric fluid movement and are used to reduce the amount of external hardware necessary to operate the microfluidic device. Generally, a micropump is active or passive. Passive micropumps rely for example on the phenomenon that small fluid volumes in contact with microstructured surfaces move spontaneously as a result of the interplay between the liquid's surface tension and the surface's chemical composition and topography in the direction that minimizes the free energies between the vapor, fluid, and solid interfaces. Alternatively, they can rely on the surface tension of droplets placed at inlets/outlets of microchannels to drive the flow. Therein, the flow rates are dictated by the curvature of the droplets, which in turn are controlled by the amount of fluid dispensed. Preferred, however, are active micropumps since they are amenable to computerized control. Active micropumps rely on an external signal to initiate and cease pumping activities. This external signal adds the ability to control the rate and temporal behavior of the pump. Preferably, the active micropumps are independently selected (i.e. the device may contain different micropumps) from the group consisting of syringe micropumps, pneumatic membrane micropumps, piezoelectric micropumps, Braille pin micropumps, electrochemical micropumps, electroosmotic micropumps, acoustic micropumps, magnetohydrodynamic micropumps, electrohydrodynamic micropumps and gas permeation micropumps; more preferably, the active micropumps are independently selected from the group consisting of syringe micropumps, pneumatic membrane micropumps and Braille pin micropumps.

Syringe micropumps are pumping devices including a syringe, i.e. a barrel, housing or similar structure that defines a cavity, chamber, or similar structure in which a piston, plunger or similar structure is slidable so as to eject a fluid there. A syringe pump allows for precise actuation of the fluids. Pneumatic membrane micropumps are generally based on an existing microvalve design with several such valves actuating in series to produce peristalsis in the microchannel. Briefly, a fluid volume ("bolus") is bound between activated pumping membranes and moves unidirectionally through sequential activation of the pumping membranes. Consequently, the bolus will move away from its initial position, generating a volume displacement in the microchannel. Piezoelectric micropumps rely on a piezoelectric device material undergoing shape changes when supplied with an electrical current. Stress exerted by the piezoelectric material, coupled to a (preferably thin) diaphragm, can be used to pump fluids. Braille pin micropumps are operated using the push-pins of a Braille display, which are programmed to operate in a peristaltic pattern. Electrochemical micropumps use gas generated from the electrolysis of an aqueous solution of e.g. $KNO_3$ to pump fluid through a microchannel. By adjusting the current amplitude and pulse using electrodes connected to a microchannel, a flow can be achieved. Electroosmotic micropumps rely on electroosmotic flow, which is the bulk motion of liquid resulting from an applied electric field across a porous material, capillary, membrane, or microchannel with charged walls. When for example a DC electric field is applied across at least two electrodes, a high force is experienced at the microchannel walls, resulting in the movement of charge and fluid through the microchannel. Acoustic micropumps rely on acoustic streaming, which refers to the phenomenon that (i) compressible fluid experiences a high-frequency oscillation driven by a source of sound, wherein the nonlinear interaction causes a steady current or (ii) incompressible fluid oscillates adjacent to an obstacle or an interface. In particular, acoustic streaming flows based on quartz wind, Eulerian streaming and Kundt's dust are suitable for microfluidic devices (see Suh and Kang on Acoustic Separation in "Encyclopedia of Microfluidics and Nanofluidics", Springer Reference, Volume 1, pages 25 to 32). Magnetohydrodynamic micropumps drive fluid flow in conductive liquids which are subjected to perpendicular applied electric and magnetic fields across a microchannel. A resulting Lorentz force is generated on the liquid perpendicular to the direction of both the electric and magnetic fields, therefore causing the fluid to be pumped through the microchannel. Electrohydrodynamic micropumps use electrowetting to manipulate discrete droplets of fluid over an array of electrodes in what is known as digital microfluidics. Electrowetting is the change in contact angle between a solid and electrolyte resulting from the application of an electric field between the two. Gas permeation micropumps operate with gas permeable microfluidic device materials, such as PDMS. The working principle is that the removal of all the residual gas that is present in the gaspermeable material (e.g. by placing the device in vacuum for 15-20 min) will create a local vacuum in the microchannels, which can pull fluid through the channels. For a review of the above microvalves and micropumps, see Au et al., Micromachines 2011, 2, 179-220.

The term "droplet generator" refers to a structure creating a stream of monodispersed water or oil droplets in an immiscible phase. Microfluidic droplet generators work by combining two or more streams of immiscible fluids and generating a shear force on the discontinuous phase causing it to break up into discrete droplets. Preferred droplet generators are focused-flow droplet generators and T-shaped droplet generators. Focused-flow droplet generators are based on a continuous phase fluid (focusing or sheath fluid) flanking or surrounding the dispersed phase (focused or core fluid), so as to give rise to droplet break-off in the vicinity of an orifice through which both fluids are extruded. T-shaped droplet generators use a microchannel T-junction, at which droplets are spontaneously formed at the intersection, taking advantage of the interface instability between oil and aqueous streams each coming from one direction towards the junction. For other methods of generating droplets, see the compartmentalisation or microencapsulation procedures described above.

The microfluidic device of the fifth aspect can exist alone or can be a part of a microfluidic system. Thus, the fifth aspect also relates to a microfluidics system, comprising:

a microfluidic device as described above, and at least one detection means for detecting at least one particle comprised in a microfluidic droplet.

Preferably, the detection means is light sensors, for example photomultiplier tubes, CMOS or CCD cameras, or detection electrodes or an imaging device, preferably real-time, capable of pattern and/or signal recognition, wherein the pattern is for example a microfluidic droplet or a particle within a microfluidic droplet. In a preferred embodiment, the imaging device comprises a camera and a unit for processing image data such as a computer.

In related embodiments, the microfluidics system may further comprise one or more of the following: one or more pumps for introducing fluids into the system and/or through the system; one or more high voltage amplifiers; detection equipment or systems such as a microscope; one or more valves; a laser spectroscopy setup including a laser light source and a light detector; data storage systems; and/or control systems for controlling fluid transport and/or direction within the device, monitoring and controlling environmental conditions to which fluids in the device are subjected, e.g., temperature, current, and the like.

In particular, the fifth aspect also relates to the use of the microfluidic device or system for carrying out the method of the first, second, third and/or fourth aspect of the invention.

The invention is described by way of the following examples which are to be construed as merely illustrative and not limitative of the scope of the invention.

EXAMPLE 1

In the first example, a combinatorial Braille-valve chip which allows mixing fluid samples in a systematic combinatorial fashion is used for mixing DNA fragments harbouring different barcode building blocks (FIG. 1). For example, a primer with specific barcode sequences can be assembled by ligation of three individual barcode fragments (BC1, BC2 and BC3). Using 8 different variants of the first fragment (BC1-1 to BC1-8; infused into the microfluidic chip through different inlets), 8 different variants of the second fragment (BC2-1 to BC2-8; also infused through different inlets) and 96 different variants of the third fragment (BC3-1 to BC3-96; infused sequentially by an autosampler) one can rapidly generate 6144 differently barcoded polyT-primers (at a throughput of 2-5 s per sample). This number can even be scaled up further, as the autosampler can feed in samples from different microtiter plates.

For barcoding, cells are encapsulated into droplets together with the fragments and a ligation mix. During incubation, the combinatorially barcoded polyT-primers are assembled. Then, the droplets are fused with a second droplet species, hosting lysis buffer and a reverse transcription mix. Subsequently, the droplets are collected and incubated in a PCR tube at 50° C. to enable the synthesis of cDNA harbouring the barcode sequences. In a next step, the droplets are broken, and the samples are pooled. All downstream procedures such as PCR and preparation of the sequencing library can subsequently be carried out in a single tube using conventional technology. The final sequencing step then reveals the transcriptome pattern of the different samples.

EXAMPLE 2

In a second example, the invention is used for genotype/phenotype correlation studies. For example, the cells can be analysed for a particular phenotype by laser spectroscopy or imaging prior to encapsulation (FIG. 2). Based on the (recorded) phenotype, a particularly barcoded primer is added thus allowing to link the finally obtained transcriptome data with this phenotype. A factor to enable this is a system fast enough to switch the microfluidic valves each time a cell passes the phenotype detector. Furthermore, even if the valves can be switched fast, the establishment of an equilibrated fluid flow (e.g. to encapsulate a different primer) typically takes much longer than the time the cell needs to travel from the detection point to the droplet maker. For this, it is advantageous to switch the valves each time after they have been encapsulated rather than before (FIG. 3): Empty droplets of a given composition (e.g. with all fragments for the synthesis of Primer A) are continuously generated. Once a cell is detected by laser spectroscopy, it is still co-encapsulated into the same sample composition, but the valves are switched just milliseconds afterwards. This ensures that the next cell passing by (and being detected) will obtain a different sample composition (e.g. all fragments for the synthesis of primer B). In case two cells are flowing through the device closely together, so that the valves cannot be switched fast enough, this incident is recorded thus allowing to exclude the particular sample from the downstream data analysis. However, by simply spacing the cells sufficiently (e.g. by dilution), this problem can be overcome in the first place. Taken together, this novel approach for single-cell genotype/phenotype correlation studies should be of special interest for analysing heterogeneous samples such as tumour cells or developing embryos.

EXAMPLE 3

In another example, the invention is used for pharmacogenomics studies: instead of analysing different cells for different phenotypes, the same kind of cells is encapsulated into droplets together with all barcoding components and different drugs (FIG. 5). These can also be fed into the microfluidic system using a (second) separate autosampler, or simply by adding the drugs to the different primer fragment samples. The latter option even allows for the analysis of combinatorial drug effects. Subsequent to encapsulation the droplets are incubated at 37° C. for a time period sufficiently long to impose a drug effect on the cells. Then, the droplets are fused with a second droplet species, hosting lysis buffer and a reverse transcription mix. Subsequently, the droplets are collected and incubated in a PCR tube at 50° C. to enable the synthesis of cDNA harbouring the barcode sequences. In a next step, the droplets are broken, and the samples are pooled. All downstream procedures such as PCR and preparation of the sequencing library can then be carried out in a single tube using conventional technology. Sequencing eventually reveals how each drug affects the cellular transcriptome. Since the assays are carried out in minute volumes (>1 nL), this method even allows to directly test the effect of many different drugs (such as a drug library) on patient-derived cells (e.g. biopsies), which are normally not amenable for drug screens. This should also have major impact on personalized therapies.

EXAMPLE 4

When preparing combinatorial mixtures on a microfluidic chip, cross-contamination between different samples should be ruled out (FIG. 6). This is not trivial, as the different components are first mixed in microfluidic channels (controlled by valves) and only subsequently encapsulated only further downstream. Hence, even when the valves close or switch to generate the next mixture, they still contain the previous sample in the downstream channel sections. In consequence, the first couple of droplets of sample composition n still contains contaminations of sample n−1. To overcome this problem, we have designed a special microfluidic chip: Downstream of the droplet maker the droplets are flushed through at least 2 branching channels (waste channel and collection channel), each controlled by a microfluidic valve. Whenever droplets of a new sample are generated, the first droplets of this kind are sent to the waste, and only afterwards (e.g. after 0.5 s) the valves are switched so that the newly generated droplets are sent to the collection channel. This way, the cross-contamination in all collected droplets is drastically reduced.

EXAMPLE 5

Barcoding cellular mRNA according to particular drug treatments. The combinatorial microfluidic chip was used to generate droplets containing the following components:
    MCF-7 cells+media+ligation mix+barcode fragment BC-1+barcode fragment BC-A+Thiostrepton
    MCF-7 cells+media+ligation mix+barcode fragment BC-2+barcode fragment BC-B+Doxorubicin treated cells
    MCF-7 cells+media+ligation mix+barcode fragment BC-1+barcode fragment BC-B The resulting emulsions were collected separately in droplet traps (as shown in Hu H et al., Lab Chip 2015) for 12 h at 37° C., before cell lysis was achieved by repeated freezing and thawing. Then the emulsion was broken and hybridized cellular mRNA was purified using streptaviding-coated beads. This step ensures that only mRNA hybridized to ligated barcode combinations (e.g. 1A for the Thiostrepton sample) is isolated. Subsequently reverse transcription was carried out and the abundance of target genes was assessed by qPCR using primers specific for the target genes. Barcode fragment combination is shown exemplary for fragments BC-A and BC-1 in FIG. 7, as well as the reverse transcription and qPCR using the barcode. Expression levels of p21 (FIG. 8A) and FoxM1 (FIG. 8B) were normalized to Actb expression and the fold change in expression was determined between treated and untreated cells. In transcriptomes labelled with the barcode combination 1A (Thiostrepton) a significant downregulation of FoxM1 expression was observed (which is in good agreement with Mol Med Rep. 2015 July; 12(1):1457-64. doi: 10.3892/mmr.2015.3469), while the sample with barcode 2B (Dox treated) showed a significant upregulation of p21 (which is in good agreement with J Biomed Sci. 2012 Feb. 4; 19:15. doi: 10.1186/1423-0127-19-15).

EXAMPLE 6

Minimizing cross-contamination by sending newly generated barcode mixtures to the waste for a pre-determined time period before collecting sample emulsions. Syringes containing ligation mix as well as barcode fragments BC-1, BC-A, BC-B, BC-C and BC-D were connected to the combinatorial microfluidic chip and injected at identical flow rates. Microfluidic braille valves controlling individual inlets were used to direct the fluids either to the waste or to the droplet maker. This way the following samples were generated:
    Ligation mix+1C->collection for 30 s
    Ligation mix+1A->waste for 30 s
    Ligation mix+1C->waste for 5 s-10 s
    Ligation mix+1C->collections for 30 s (=test sample)

The test sample was then analyzed for contaminations with barcode BC-A using BC-A-specific taqman probes. First a standard curve (FIG. 9A) was prepared using different ratios of BC-A (X-axis) spiked into the BC-C solution. This information was then used to estimate the BC-A cross contamination in the test sample (FIG. 9B). As expected, sending the newly generated test sample to the waste (for time periods as indicated on the X-axis) ensured to have only minimal cross-contaminations, typically below 1%.

The invention claimed is:
1. A method for co-localizing a particle comprising DNA and/or RNA with a known barcode oligonucleotide or set of components thereof in a microfluidic droplet in a microfluidics system, comprising:
    (i) feeding a particle comprising DNA and/or RNA into a co-localizing channel,
    (ii) passing the particle past a series of at least two valve-operated oligonucleotide inlets or sets of valve-operated oligonucleotide inlets, wherein one of the at least two oligonucleotide inlets or sets of oligonucleotide inlets is open while the particle passes it, and wherein each oligonucleotide inlet, when open, feeds a known barcode oligonucleotide or set of components thereof into the co-localizing channel, or each set of oligonucleotide inlets, when open, feeds a set of components of a known barcode oligonucleotide into the co-localizing channel, and
    (iii) closing the oligonucleotide inlet or set of oligonucleotide inlets that is open after the particle has passed it and opening a different oligonucleotide inlet or set of oligonucleotide inlets of the at least two valve-operated oligonucleotide inlets or sets of valve-operated oligonucleotide inlets,
wherein
    (A) the particle of step (i) and the known barcode oligonucleotide or the set of components thereof of step (ii) are fed into the co-localizing channel while not comprised in microfluidic droplets, and the method further comprises generating microfludic droplets downstream of the at least two valve-operated oligonucleotide inlets or sets of oligonucleotide inlets prior, during or after step (iii), including a microfluidic droplet comprising the particle and the known barcode oligonucleotide or components thereof, or
    (B) the particle of step (i) and the known barcode oligonucleotide or the set of components thereof of step (ii) are fed into the co-localizing channel comprised in microfluidic droplets and these microfluidic droplets are fused.

2. The method of claim 1, comprising repeating all steps one or more times with a further particle after step (i) is carried out for the particle fed into the co-localizing channel prior to this further particle, wherein for each particle passing the series of at least two valve-operated oligonucleotide inlets or sets of valve-operated oligonucleotide inlets in step (ii), a different valve-operated oligonucleotide inlet or set of valve-operated oligonucleotide inlets is open, and wherein the barcode oligonucleotide or set of components thereof fed into the co-localizing channel while the particle passes the series is predetermined or recorded.

3. The method of claim 1, further comprise detecting the particle at a detection point in the co-localizing channel.

4. The method of claim 3, wherein the particle is a cell and the cell is phenotyped at the detection point.

5. The method of claim 1, comprising feeding a drug into the co-localizing channel (a) via the oligonucleotide inlet or at least one oligonucleotide inlet of the set of oligonucleotide inlets together with the barcode oligonucleotide or components thereof, or (b) via one of at least two drug inlets which opens and closes together with the oligonucleotide inlet or set of oligonucleotide inlets and is located adjacent to the oligonucleotide inlet or set of oligonucleotide inlets or within the set of oligonucleotide inlets; or opens when the particle passes the drug inlet and closes once it has passed it.

6. The method of any claim 1, wherein the known barcode oligonucleotide is generated in the microfluidics system and generating the known barcode oligonucleotide comprises:
I. (a) feeding a first oligonucleotide into an oligonucleotide channel terminating at a oligonucleotide inlet of a set of the at least two sets of oligonucleotide inlets, wherein the first oligonucleotide comprises a priming region or alternatively inverted repeats of transposable elements, a variable region and a single-stranded annealing region,
(b) optionally feeding one or more sequential internal oligonucleotides into a further oligonucleotide channel, each oligonucleotide channel terminating at a further oligonucleotide inlet of the set of (a), wherein each sequential internal oligonucleotide comprises a variable region between two single-stranded annealing regions,
(c) feeding a terminal oligonucleotide into a further oligonucleotide channel terminating at a further oligonucleotide inlet of the set of (a), wherein the terminal oligonucleotide comprises a single-stranded annealing region, a variable region and optionally a priming region or alternatively inverted repeats of transposable elements,
wherein the single-stranded annealing regions are overlapping complementary sequences enabling the annealing of the first oligonucleotide, the optional one or more sequential internal oligonucleotides, and the terminal oligonucleotide in this order into a single linear oligonucleotide,
(d) annealing the first oligonucleotide, the optional one or more sequential internal oligonucleotides, and the terminal oligonucleotide together in this order into a single linear and at least partially double-stranded oligonucleotide via the overlapping annealing regions downstream of the oligonucleotide inlets,
(e) optionally, if the single linear oligonucleotide is partially double-stranded, extending double-stranded portions of the partially double-stranded oligonucleotide and/or filling gaps in the partially double-stranded oligonucleotide enzymatically, and
(f) ligating the annealed first oligonucleotide, the optional one or more sequential internal oligonucleotides, and the terminal oligonucleotide, or, if the first oligonucleotide is annealed directly to the terminal nucleotide, extending double-stranded portions of the resulting partially double-stranded oligonucleotide; or
II. (a) feeding a first oligonucleotide into an oligonucleotide combination channel terminating at one of the at least two valve-operated oligonucleotide inlets, wherein the first oligonucleotide comprises a priming region or alternatively inverted repeats of transposable elements, a variable region and a single-stranded annealing region,
(b) optionally feeding one or more sequential internal oligonucleotides into the oligonucleotide combination channel, wherein each sequential internal oligonucleotide comprises a variable region between two single-stranded annealing regions,
(c) feeding a terminal oligonucleotide into the oligonucleotide combination channel, wherein the terminal oligonucleotide comprises a single-stranded annealing region, a variable region and optionally a priming region or alternatively inverted repeats of transposable elements, wherein the single-stranded annealing regions are overlapping complementary sequences enabling the linking of the first oligonucleotide, the optional one or more sequential internal oligonucleotides, and the terminal oligonucleotide in this order into a single linear oligonucleotide, and
(d) annealing the first oligonucleotide, the optional one or more sequential internal oligonucleotides, and the terminal oligonucleotide together in this order into a single linear and at least partially double-stranded oligonucleotide via the overlapping annealing regions downstream of the oligonucleotide inlets, and
(e) optionally, if the single linear oligonucleotide is partially double-stranded, extending double-stranded portions of the partially double-stranded oligonucleotide and/or filling gaps in the partially double-stranded oligonucleotide enzymatically, and
(f) ligating the annealed first oligonucleotide, the optional one or more sequential internal oligonucleotides, and the terminal oligonucleotide, or, if the first oligonucleotide is annealed directly to the terminal nucleotide, extending double-stranded portions of the resulting partially double-stranded oligonucleotide.

7. The method of claim 6, wherein:
in (a) the first oligonucleotide is chosen from one of at least two first oligonucleotides having the same optional priming region or alternatively inverted repeats of transposable elements, different variable regions and the same annealing region,
in (b) the one or more sequential internal oligonucleotide are each chosen from at least two internal oligonucleotides having different variable regions and the same annealing regions, wherein the annealing regions differ between sequential internal oligonucleotides, and
in (c) the terminal oligonucleotide is chosen from one of at least two terminal oligonucleotides having the same annealing region, different variable regions and the same optional priming region or alternatively inverted repeats of transposable elements.

8. The method of claim 1, further comprising fusing the microfluidic droplet comprising the particle comprising DNA and/or RNA and the barcode oligonucleotide or set of components thereof with a microfluidic droplet comprising one or more of: a ligation mix, a primer extension mix, a reverse transcription mix (RT), a PCR mix, an RT-PCR mix, a transposition mix and/or a lysis buffer.

9. The method of claim 1, further comprising:
(i) sending the microfluidic droplet comprising the particle and the known barcode oligonucleotide or components thereof into a collection channel forming a junction with a waste channel downstream of the co-localizing channel, using a channel selection means, sending at least a portion of the following microfluidic droplets comprising the known barcode oligonucleotide or components thereof into the waste channel using the channel selection means, wherein the channel selection means selects the collection channel before a further microfluidic droplet comprising (i) a particle comprising DNA and/or RNA and (ii) not the same known barcode oligonucleotide arrives at the junction of the collection and waste channel, and wherein the valves of the collection and waste channel are operatively linked to the valves of the oligonucleotide inlets such that microfluidic droplets comprising more than one barcode oligonucleotide or components for more than one barcode oligonucleotide are sent to the waste channel; or (ii) closing the inlet that feeds the particles into the microfluidic channel for a time to avoid particles passing the series of oligonucleotide inlets at the time when one of the oligonucleotide inlets closes and another opens, to avoid the generation of microfluidic droplets comprising a particle and more than one barcode oligonucleotide or components for more than one barcode oligonucleotide.

10. A method for barcoding the transcriptome of a cell, for barcoding a DNA amplificate from a cell or for barcoding the genome of a cell, comprising the steps of
(i) co-localizing a cell with a known barcode oligonucleotide in a microfluidic droplet using the method of claim 1,
(ii) lysing the cell in the microfluidic droplet,
(iii) annealing the barcode oligonucleotide to RNA or DNA of the lysed cell in the microfluidic droplet,
(iv) carrying out a reverse transcription (RT), RT-PCR, PCR, or a transposition reaction using the annealed barcode oligonucleotide as primer(s) or transposable elements, respectively, in the microfluidic droplet or in an aqueous phase in which the microfluidic droplet is disrupted, thereby generating a barcoded transcriptome, DNA amplificate or genome,
wherein an RT mix, an RT-PCR mix, a PCR mix, or a transposition mix, respectively, is comprised in the co-localizing channel in step (i), is comprised in a microfluidic droplet fused to the microfluidic droplet of step (i), (ii) or (iii) or is comprised in an aqueous phase in which the microfluidic droplet is disrupted.

11. The method of claim 10, further comprising the steps of:
(v) inactivating any enzymes of the microfluidic droplet comprising the barcode oligonucleotide and disrupting the microfluidic droplet, in any order, and
(vi) analyzing the barcoded transcriptome, barcoded DNA amplificate, or barcoded genome.

12. The method of claim 11, wherein the microfluidic droplet is pooled with one or more further microfluidic droplets after step (iii) or (iv), or the contents of the microfluidic droplet are pooled with the contents of one or more further microfluidic droplets between step (iii), (iv) or (v), wherein the one or more further microfluidic droplets are generated with the same method carried out with a different barcode oligonucleotide each, and wherein the transcriptomes or DNA amplificates of all microfluidic droplets is/are analyzed in parallel.

13. A method for correlating the phenotype of a single cell with its transcriptome, with a DNA amplificate derived from the cell or with its genome, comprising barcoding the transcriptome of a single cell, barcoding a DNA amplificate from a single cell or barcoding the genome of a single cell using the method of claim 10, wherein the cell is phenotyped in step (i), and wherein the sequence of the barcode in the barcoded transcriptome, amplificate or genome indicates the phenotype of the cell from which the transcriptome, DNA amplificate or genome is derived.

14. A method for determining the effect of a drug on the transcriptome of a cell or on a DNA amplificate from a cell, comprising barcoding a transcriptome of a cell or a DNA amplificate from a cell using the method of claim 10, wherein the DNA amplificate is generated from mRNA by RT-PCR, wherein a known drug is fed into the microchannel in step (i), and wherein the sequence of the barcode in the barcoded transcriptome or the barcoded DNA amplificate indicates the drug to which the cell was exposed or the cell which was exposed to the drug.

* * * * *